(12) United States Patent
Cunningham et al.

(10) Patent No.: US 7,301,628 B2
(45) Date of Patent: Nov. 27, 2007

(54) METHOD AND APPARATUS FOR DETECTING BIOMOLECULAR INTERACTIONS

(75) Inventors: Brian T. Cunningham, Champaign, IL (US); Peter Y. Li, Andover, MA (US); Frank DiFilippi, Bilerica, MA (US)

(73) Assignee: SRU Biosystems, Inc., Woburn, MA (US)

(*) Notice: Subject to any disclaimer, the term of this patent is extended or adjusted under 35 U.S.C. 154(b) by 0 days.

(21) Appl. No.: 11/404,430

(22) Filed: Apr. 13, 2006

(65) Prior Publication Data

US 2006/0181705 A1    Aug. 17, 2006

Related U.S. Application Data

(60) Division of application No. 10/180,647, filed on Jun. 26, 2002, which is a continuation-in-part of application No. 09/930,352, filed on Aug. 15, 2001, and a continuation-in-part of application No. 10/059,060, filed on Jan. 28, 2002, now Pat. No. 7,070,987, and a continuation-in-part of application No. 10/058,626, filed on Jan. 28, 2002, now Pat. No. 6,951,715.

(60) Provisional application No. 60/244,312, filed on Oct. 30, 2000, provisional application No. 60/283,314, filed on Apr. 12, 2001, provisional application No. 60/303,028, filed on Jul. 3, 2001.

(51) Int. Cl.
*G01J 3/28* (2006.01)

(52) U.S. Cl. .................. 356/326; 356/445
(58) Field of Classification Search ........... 356/326, 356/445
See application file for complete search history.

(56) References Cited

U.S. PATENT DOCUMENTS 3,689,346 A    9/1972    Rowland ............ 156/245

(Continued)

FOREIGN PATENT DOCUMENTS

CA    2394966    8/2001

(Continued)

OTHER PUBLICATIONS

U.S. Appl. No. 60/244,312, filed Oct. 30, 2000, Cunningham et al.

(Continued)

*Primary Examiner*—Gregory J. Toatley, Jr.
*Assistant Examiner*—Kara Geisel
(74) *Attorney, Agent, or Firm*—McDonnell Boehnen Hulbert & Berghoff LLP

(57) ABSTRACT

Method and apparatus for detecting biomolecular interactions. The use of labels is not required and the methods may be performed in a high-throughput manner. An apparatus for detecting biochemical interactions occurring on the surface of a biosensor includes a light source. A first optical fiber is coupled to the light source and illuminates the biosensor. A second optical fiber detects a wavelength reflected from the biosensor. A spectrometer determines spectra of a reflected signal from the biosensor.

7 Claims, 16 Drawing Sheets

U.S. PATENT DOCUMENTS

| | | | |
|---|---|---|---|
| 4,240,751 A | 12/1980 | Linnecke et al. | 356/409 |
| 4,289,371 A | 9/1981 | Kramer | 350/3.71 |
| 4,344,438 A | 8/1982 | Schultz | 128/633 |
| 4,420,502 A | 12/1983 | Conley | 427/54.1 |
| 4,536,608 A | 8/1985 | Sheng et al. | |
| 4,560,248 A | 12/1985 | Cramp et al. | 385/12 |
| 4,576,850 A | 3/1986 | Martens | |
| 4,608,344 A | 8/1986 | Carter et al. | 436/34 |
| 4,650,329 A | 3/1987 | Barrett et al. | 356/481 |
| 4,652,290 A | 3/1987 | Cho et al. | 65/31 |
| 4,668,558 A | 5/1987 | Barber | |
| 4,701,008 A | 10/1987 | Richard et al. | 385/132 |
| 4,810,658 A | 3/1989 | Shanks et al. | 436/172 |
| 4,815,843 A | 3/1989 | Tiefenthaler et al. | 356/128 |
| 4,818,710 A | 4/1989 | Sutherland et al. | 436/527 |
| 4,857,273 A | 8/1989 | Stewart et al. | 436/82 |
| RE33,064 E | 9/1989 | Carter | 436/34 |
| 4,876,208 A | 10/1989 | Gustafson et al. | 436/531 |
| 4,882,288 A | 11/1989 | North et al. | 436/525 |
| 4,888,260 A | 12/1989 | Cowan | 403/1 |
| 4,931,384 A | 6/1990 | Layton et al. | 435/7 |
| 4,952,056 A | 8/1990 | Tiefenthaler | 356/73.1 |
| 4,958,895 A | 9/1990 | Wells et al. | 350/96.12 |
| 4,992,385 A | 2/1991 | Godfrey | 436/525 |
| 4,999,234 A | 3/1991 | Cowen | 428/156 |
| 5,071,248 A | 12/1991 | Tiefenthaler et al. | 356/128 |
| 5,118,608 A | 6/1992 | Layton et al. | 435/7.1 |
| 5,155,785 A | 10/1992 | Holland et al. | 385/89 |
| 5,156,785 A | 10/1992 | Zdrahala | 264/108 |
| 5,170,448 A | 12/1992 | Ackley et al. | 385/31 |
| 5,175,030 A | 12/1992 | Lu et al. | 428/30 |
| 5,210,404 A | 5/1993 | Cush et al. | 250/216 |
| 5,229,614 A | 7/1993 | Anderson et al. | 250/370.12 |
| 5,242,828 A | 9/1993 | Bergström et al. | 435/291 |
| 5,268,782 A | 12/1993 | Wenz et al. | 359/81 |
| 5,310,686 A | 5/1994 | Sawyers et al. | |
| 5,337,183 A | 8/1994 | Rosenblatt | 359/248 |
| 5,413,884 A | 5/1995 | Koch et al. | 430/5 |
| 5,442,169 A | 8/1995 | Kunz | 250/227.21 |
| 5,455,178 A | 10/1995 | Fattinger | 436/164 |
| 5,475,780 A | 12/1995 | Mizrahi | 385/37 |
| 5,478,527 A | 12/1995 | Gustafson et al. | 422/82 |
| 5,478,756 A | 12/1995 | Gizeli et al. | 436/527 |
| 5,492,840 A | 2/1996 | Malmquist et al. | |
| 5,496,701 A | 3/1996 | Pollard-Knight | 435/7.4 |
| 5,559,338 A | 9/1996 | Elliot et al. | 250/492.1 |
| 5,598,267 A | 1/1997 | Sambles et al. | 356/369 |
| 5,598,300 A | 1/1997 | Magnusson et al. | 359/566 |
| 5,606,170 A | 2/1997 | Saaski et al. | 250/458.1 |
| 5,615,052 A | 3/1997 | Doggett | 359/811 |
| 5,629,214 A | 5/1997 | Crosby | 436/518 |
| 5,631,171 A | 5/1997 | Sandstrom et al. | 436/518 |
| 5,690,894 A | 11/1997 | Pinkel et al. | 422/68.1 |
| 5,691,846 A | 11/1997 | Benson et al. | 359/530 |
| 5,732,173 A | 3/1998 | Bylander et al. | 385/49 |
| 5,738,825 A | 4/1998 | Rudigier et al. | 422/82 |
| 5,768,461 A | 6/1998 | Svetkoff et al. | 385/116 |
| 5,771,328 A | 6/1998 | Wortman et al. | 385/146 |
| 5,792,411 A | 8/1998 | Morris et al. | 264/400 |
| 5,801,390 A | 9/1998 | Shiraishi | 250/559.3 |
| 5,804,453 A | 9/1998 | Chen | |
| 5,814,516 A | 9/1998 | Vo-Dinh | 435/287.2 |
| 5,814,524 A | 9/1998 | Walt et al. | 436/514 |
| 5,821,343 A | 10/1998 | Keogh | |
| 5,846,843 A | 12/1998 | Simon | |
| 5,864,641 A | 1/1999 | Murphy et al. | 385/12 |
| 5,922,550 A | 7/1999 | Everhart et al. | 435/7.21 |
| 5,925,878 A | 7/1999 | Challener | |
| 5,955,335 A | 9/1999 | Thust et al. | |
| 5,955,378 A | 9/1999 | Challener | |
| 5,986,762 A | 11/1999 | Challener | |
| 5,991,480 A | 11/1999 | Kunz et al. | |
| 5,994,150 A | 11/1999 | Challener et al. | |
| 5,998,298 A | 12/1999 | Hetherington et al. | |
| 6,035,089 A | 3/2000 | Grann et al. | |
| 6,042,998 A | 3/2000 | Brueck et al. | |
| 6,052,213 A | 4/2000 | Burt et al. | 359/237 |
| 6,076,248 A | 6/2000 | Hoopman et al. | |
| 6,088,505 A | 7/2000 | Hobbs | |
| 6,100,991 A | 8/2000 | Challener | |
| 6,128,431 A | 10/2000 | Siminovitch | 385/147 |
| 6,146,593 A | 11/2000 | Pinkel et al. | 422/68.1 |
| 6,174,677 B1 * | 1/2001 | Vo-Dinh | 356/301 |
| 6,185,019 B1 | 2/2001 | Hobbs et al. | 359/30 |
| 6,200,737 B1 | 3/2001 | Walt et al. | 430/320 |
| 6,215,928 B1 | 4/2001 | Friesem et al. | 385/37 |
| 6,218,194 B1 | 4/2001 | Lyndin et al. | 436/518 |
| 6,235,488 B1 | 5/2001 | Tom-Moy et al. | |
| 6,303,179 B1 | 10/2001 | Koulik et al. | |
| 6,316,153 B1 | 11/2001 | Goodman et al. | 430/8 |
| 6,320,991 B1 | 11/2001 | Challener et al. | |
| RE37,473 E | 12/2001 | Challener | |
| 6,338,968 B1 | 1/2002 | Hefti | |
| 6,340,598 B1 | 1/2002 | Herron et al. | |
| 6,346,376 B1 | 2/2002 | Sigrist et al. | |
| 6,377,721 B1 | 4/2002 | Walt et al. | 385/12 |
| 6,404,554 B1 | 6/2002 | Lee et al. | 359/576 |
| 6,449,097 B1 | 9/2002 | Zhu et al. | 359/576 |
| 6,558,957 B1 | 5/2003 | Roinestad et al. | 422/82.05 |
| 6,570,657 B1 | 5/2003 | Hoppe et al. | 356/445 |
| 6,579,673 B2 | 6/2003 | McGrath et al. | 435/5 |
| 6,587,276 B2 | 7/2003 | Daniell | 359/622 |
| 6,661,952 B2 | 12/2003 | Simpson et al. | 385/37 |
| 6,667,159 B1 * | 12/2003 | Walt et al. | 422/82.08 |
| 6,707,561 B1 | 3/2004 | Budach et al. | 356/521 |
| 6,748,138 B2 | 6/2004 | Wang et al. | 385/37 |
| 6,902,703 B2 | 6/2005 | Marquiss et al. | |
| 7,023,544 B2 | 4/2006 | Cunningham et al. | 356/326 |
| 7,094,595 B2 | 8/2006 | Cunningham et al. | 435/287.2 |
| 7,118,710 B2 | 10/2006 | Cunningham | 422/82.09 |
| 7,142,298 B2 | 11/2006 | Nuspliger | 356/326 |
| 7,148,964 B2 | 12/2006 | Cunningham et al. | 358/326 |
| 7,158,230 B2 | 1/2007 | Cunningham et al. | 356/326 |
| 7,170,599 B2 | 1/2007 | Cunningham et al. | 356/326 |
| 2002/0018610 A1 | 2/2002 | Challener et al. | |
| 2002/0123050 A1 | 9/2002 | Poponin | 356/301 |
| 2002/0127565 A1 | 9/2002 | Cunningham et al. | |
| 2002/0135752 A1 | 9/2002 | Sokolov et al. | 356/39 |
| 2002/0168295 A1 | 11/2002 | Cunningham et al. | |
| 2002/0170145 A1 | 11/2002 | Perraut | |
| 2003/0003599 A1 | 1/2003 | Wagner et al. | |
| 2003/0017580 A1 | 1/2003 | Cunningham et al. | |
| 2003/0017581 A1 | 1/2003 | Li et al. | |
| 2003/0026891 A1 | 2/2003 | Qiu et al. | |
| 2003/0027327 A1 | 2/2003 | Cunningham et al. | |
| 2003/0027328 A1 | 2/2003 | Cunningham et al. | |
| 2003/0032039 A1 | 2/2003 | Cunningham et al. | |
| 2003/0059855 A1 | 3/2003 | Cunningham et al. | |
| 2003/0068657 A1 | 4/2003 | Lin et al. | |
| 2003/0077660 A1 | 4/2003 | Pien et al. | |
| 2003/0092075 A1 | 5/2003 | Pepper | |
| 2003/0113766 A1 | 6/2003 | Pepper et al. | |
| 2003/0148542 A1 | 8/2003 | Pawlak | |
| 2003/0210396 A1 | 11/2003 | Hobbs et al. | 356/416 |
| 2004/0011965 A1 | 1/2004 | Hodgkinson | 356/317 |
| 2004/0132172 A1 | 7/2004 | Cunningham et al. | |
| 2004/0132214 A1 | 7/2004 | Lin et al. | |
| 2004/0151626 A1 | 8/2004 | Cunningham et al. | |
| 2006/0193550 A1 | 8/2006 | Wawro et al. | 385/12 |
| 2007/0041012 A1 | 2/2007 | Cunningham et al. | 356/326 |

| | | |
|---|---|---|
| 2007/0070355 A1 | 3/2007 | Cunningham ............... 356/454 |

FOREIGN PATENT DOCUMENTS

| | | |
|---|---|---|
| CA | 2395318 | 8/2001 |
| CH | 6 690 50 A5 | 2/1989 |
| CH | 6 705 21 A5 | 6/1989 |
| EP | 0 075 353 | 3/1983 |
| EP | 0 112 721 | 7/1984 |
| EP | 0 326 219 | 1/1989 |
| EP | 0 517 777 | 5/1996 |
| EP | 0 660 924 | 9/1999 |
| FR | 2 801 977 | 12/1999 |
| GB | 2 156 970 A | 10/1985 |
| GB | 2 227 089 | 7/1990 |
| WO | WO 81/00912 | 2/1981 |
| WO | WO 84/02578 | 7/1984 |
| WO | WO 86/07149 | 12/1986 |
| WO | WO 90/08313 | 7/1990 |
| WO | WO 91/13339 | 9/1991 |
| WO | WO 92/04653 | 3/1992 |
| WO | WO 92/21768 | 12/1992 |
| WO | WO 93/14392 | 7/1993 |
| WO | WO 95/03538 | 2/1995 |
| WO | WO 98/57200 | 12/1998 |
| WO | WO 99/09392 | 2/1999 |
| WO | WO 99/09396 | 2/1999 |
| WO | WO 99/54714 | 10/1999 |
| WO | WO 99/66330 | 12/1999 |
| WO | WO 00/23793 | 4/2000 |
| WO | WO 00/29830 | 5/2000 |
| WO | WO 01/04697 | 1/2001 |
| WO | WO 02/061429 | 8/2002 |

OTHER PUBLICATIONS

U.S. Appl. No. 60/283,314, filed Apr. 12, 2001, Cunningham et al.
U.S. Appl. No. 60/303,028, filed Jul. 3, 2001, Cunningham et al.
Brecht, et al., "Optical probes and transducers", *Biosensors & Bioelectronics* vol. 10, pp. 923-936 (1995).
Challener, et al., "A multilayer grating-based evanescent wave sensing technique", *Sensors and Actuators B*, 71, pp. 42-46 (2000).
Cowan, "Aztec surface-relief volume diffractive structure", *J. Opt. Soc. Am.*, vol. 7, No. 8, pp. 1529-1544 (1990).
Cowan, "Holographic honeycomb microlens", *Optical Engineering*, vol. 24, No. 5, pp. 796-802 (1985).
Cowan, "The Recording and Large Scale Replication of Crossed Holographic Grating Arrays using Multiple Beam Interferometry", *SPIE* vol. 503, Application, Theory, and Fabrication of Periodic Structures, pp. 120-129 (1984).
Cowan, et al., "The Recording and Replication of Holographic Micropatterns for the Ordering of Photographic Emulsion Grains in Film Systems", *J. Imaging Sci.*, vol. 31, No. 3, pp. 100-107 (1987).
Cunningham, B. et al., "A plastic colorimetric resonant optical biosensor for multiparallel detection of label-free biochemical interactions", *Sensors and Actuators* B 85; pp. 219-226 (2002).
Cunningham, B. et al., "Colorimetric resonant reflection as a direct biochemical assay technique", *Sensors and Actuators* B 81; pp. 316-328 (2002).
Cunningham, "Optically Based Energy Transduction", *Techniques in Analytical Chemistry*, pp. 260-291.
Hobbs, et al., "Automated Interference Lithography Systems for Generation of Sub-Micron Feature Size Patterns", *SPIE*, vol. 3879, pp. 124-135, (1999).
Huber, et al., "Direct optical immunosensing sensitivity and selectivity)", *Sensors and Actuators* B, 6, pp. 122-126 (1992).
Jenison, et al., "Interference-based detection of nucleic acid targets on optically coated silicon", *Nature Biotechnology*, vol. 19, pp. 62-64 (2001).
Jin, et al., "A biosensor concept based on imaging ellipsometry for visualization of biomolecular interactions", *Analytical Biochemistry*, vol. 232, pp. 69-72 (1995).
Jordan, et al., "Surface Plasmon Resonance Imaging Measurements of Electrostatic Biopolymer Adsorption onto Chemically Modified Gold Surfaces", *Analytical Chemistry*, vol. 69, No. 7, pp. 1449-1456 (1997).
Lin, et al., "A Porous Silicon-Based Optical Interferometric Biosensor", *Science*, vol. 278, pp. 840-843 (1997).
Magnusson, et al., "New principle for optical filters", *Appl. Phys. Lett.*, vol. 61, No. 9, pp. 1022-1024 (1992).
Magnusson, et al., "Transmission bandpass guided-mode resonance filters", *Applied Optics*, vol. 34, No. 35, pp. 8106-8109 (1995).
Morhard, et al., "Immobilization of antibodies in micropatterns for cell detection by optical diffraction", *Sensors and Actuators* B 70, pp. 232-242 (2000).
Pandey, et al., "Proteomics to study genes and genomes", *Nature* 405(6788):837-46 (2000).
Patel, et al., "Electrically tuned and polarization insensitive Fabry-Perot etalon with a liquid-crystal film", *Appl. Phys. Lett.*, vol. 58, No. 22, pp. 2491-2493 (1991).
Bertoni, et al., "Frequency-Selective Reflection and Transmission by a Periodic Dielectric Layer", *IEEE Transactions on Antennas and Propagation*, vol. 37, No. 1, pp. 78-83 (1989).
Brundrett, et al., "Normal-incidence guided-mode resonant grating filters: design and experimental demonstration", *Optics Letters*, vol. 23, No. 9, pp. 700-702 (1998).
Peng, "*Polarization-control Components and Narrow-band Filters Based on Subwavelength Grating Structures*" 1996.
Statement of Applicants dated May 10, 2004.
Leanu, Torben, *Material, Silicon Nitride*, 1996, 97, 98.
Cerac, Technical publications: *Tantalum Oxide, $Ta_2O_5$ for Optical Coating*, 2000, Cerac, Inc.
Neuschafer et al., Evanescent resonator chips: a universal platform with superior sensitivity for fluorescence-based microarrays. Biosensors & Bioelectronics, 18 (2003) 489-497.
Budach et al., Generation of transducers for fluorescence-based microarrays with enhanced sensitivity and their application for gene expression profiling. Analytical Chemistry. Jun. 1, 2003;75(11):2571-7.
Anderson, et al., "Proteomics: applications in basic and applied biology", *Current Opinion in Biotechnology*, 2000, 11:408-412.
MacBeath, et al., "Printing Proteins as Microarrays for High-Throughput Function Determination", *Science*, vol. 289, pp. 1760-1763, 2000.
deWildt, et al., "Antibody arrays for high-throughput screening of antibody-antigen interactions", *Nature Biotechnology*, vol. 18, pp. 989-994, 2000.
Cunningham, et al., "A plastic colorimetric resonant optical biosensor for multiparallel detection of label-free biochemical interactions", *Sensors and Actuators B*, 85 (2002) 219-226.
Caruso, et al., "Quartz Crystal Microbalance Study of DNA Immobilization and Hybridization for Nucleic Acid Sensor Development", *Analytical Chemistry*, vol. 69, No. 11, pp. 2043-2049, 1997.
Hefti, et al, "Sensitive detection method of dielectric dispersions in aqueous-based, surface-bound macromolecular structures using microwave spectroscopy", *Applied Physics Letters*, vol. 75, No. 12, pp. 1802-1804, 1999.
Wu, et al., "Bioassay of prostate-specific antigen (PSA) using microcantilevers", *Nature Biotechnology*, vol. 19, pp. 856-860, 2001.
Wasserman, et al., "Structure and Reactivity of Alkylsiloxane Monoloayers Formed by Reaction of Alkyltricholorosilanes on Silicon Substrates", *Langmuir*, 5, 1074-1087, 1989.
Kallury, et al., "X-ray Photoelectron Spectroscopy of Silica Surfaces Treated with Polyfunctional Silanes", *Anal. Chem.*, 60, 169-172, 1988.
Cunningham, et al., "Colorimetric resonant reflection as a direct biochemical assay technique", *Sensors and Actuators B*, 81 (2002) 316-328.
Mullaney, et al., "Epitope Mapping of Neutralizing Botulinum Neurotoxin A Antibodies by Phage Display", *Infection and Immunity*, vol. 69, No. 10, pp. 6511-6514, 2001.
Nellen, et al., "Integrated Optical Input Grating Couplers as Biochemical Sensors", *Sensors and Actuators*, 15 (1988) 285-295.

Lukosz and Tiefenthaler, "Embossing technique for fabricating integrated optical components in hard inorganic waveguiding materials," *Optics Letters*, vol. 8, pp. 537-539 (1983).

Tiefenthaler and Lukosz, "Integrated optical switches and gas sensors," *Optics Letters*, vol. 10, pp. 137-139 (1984).

Chabay, "Optical Waveguides," *Analytical Chemistry*, vol. 54, pp. 1071A-1080A (1982).

Sutherland et al., "Optical Detection of Antibody-Antigen Reactions at a Glass-Liquid Interface," *Clin. Chem.*, vol. 30, pp. 1533-1538 (1984).

Holm and Palik, "Internal-reflection spectroscopy," *Laser Focus*, vol. 15, pp. 60-65 (Aug. 1979).

Harrick and Loeb, "Multiple Internal Reflection Fluorescence Spectrometry," *Analytical Chemistry*, vol. 45, pp. 687-691 (1973).

Tien, "Light Waves in Thin Films and Integrated Optics," *Applied Optics*, vol. 10, pp. 2395-2413 (1971).

Dakss et al., "Grating Coupler for Efficient Excitation of Optical Guided Waves in Thin Films," *Applied Physics Letters*, vol. 16, pp. 523-525 (1970).

Sutherland et al., "Immunoassays at a Quartz-Liquid Interface: Theory, Instrumentation and Preliminary Application to the Fluorescent Immunoassay of Human Immunoglobulin G," *Journal of Immunological Methods*, vol. 74, pp. 253-265 (1984).

English translation of CH 670 521 A5.

English translation of CH 669 050 A5.

Patel, et al., "Multi-vwavelength Tunable Liquid-Crystal Etalon Filter", *IEEE Photonics Technology Letters*, vol. 3, No. 7, pp. 643-644 (1991).

Patterson, S.D., "Proteomics: the industrialization of protein chemistry", *Current Opinions in Biotechnology*. 11(4):413-8 (2000).

Peng, et al., "Experimental demonstration of resonant anomalies in diffraction from two-dimensional gratings", *Optics Letters* vol. 21, No. 8, pp. 549-551 (1996).

Peng, et al., "Resonant scattering from two-dimensional gratings", *J. Opt. Soc. Am. A.*, vol. 13, No. 5, pp. 993-1005 (1996).

Raguin, et al., "Structured Surfaces Mimic Coating Performance", *Laser Focus World*, pp. 113-117 (1997).

Sigal, et al., "A Self-Assembled Monolayer for the Binding and Study of Histidine-Tagged Proteins by Surface Plasmon Resonance", *Analytical Chemistry*, vol. 68, No. 3, pp. 490-497 (1996).

Wang, et al., "Design of waveguide-grating filters with symmetrical line shapes and low sidebands", *Optical Society of America*, vol. 19, No. 12, 919-921 (1994).

Wang, et al., "Guided-mode resonances in planar dielectric-layer diffraction gratings", *J. Opt. Soc. Am.*, vol. 7, No. 8, pp. 1470-1474 (1990).

Wang, et al., "Theory and applications of guided-mode resonance filter", *Applied Optics*, vol. 32, No. 14, pp. 2606-2613 (1993).

International Search Report for foreign counterpart application PCT/US01/50723, Sep. 17, 2002.

International Search Report for foreign counterpart application PCT/US03/01175, Aug. 18, 2003.

Invitation to Pay Additional Fees in foreign counterpart application PCT/US01/50723, Aug. 30, 2002.

Haidner, "Zero-Order Gratings Used as an Artificial Distributed Index Medium", *Optik, Wissenschaftliche Verlag GmbH*, Stuttgart, DE, vol. 89, No. 3, pp. 107-112, 1992.

Peng, et al., "Experimental Demonstration of Resonant Anomalies in Diffraction from two-Dimensional Gratings", *Optics Letters, Optical Society of America*, vol. 21, No. 9, pp. 549-551, 1996.

Wilson, et al., "The Optical Properties 1-19 of 'Moth Eye' Antireflection Surfaces", *Optica ACTA*, vol. 29, No. 7, pp. 993-1009, 1982.

Bagnich, et al., "*Tunable Optical Filter*", Derwent Publications, English Translation, Abstract Only, Derwent Publications Ltd.

*Corning, Inc. v. SRU Biosystems, Inc.*, Memorandum Opinion dated Nov. 15, 2005 in the United States District Court for the district of Delaware.

Liu, et al., "*Development of an optical fiber lactate sensor*", Mikrochimica Acta, 1999, 131(1-2), pp. 129-135.

U.S. Appl. No. 11/506,639, filed Aug. 18, 2006.

Amendment dated May 4, 2007 in U.S. Appl. No. 11/506,639.

\* cited by examiner

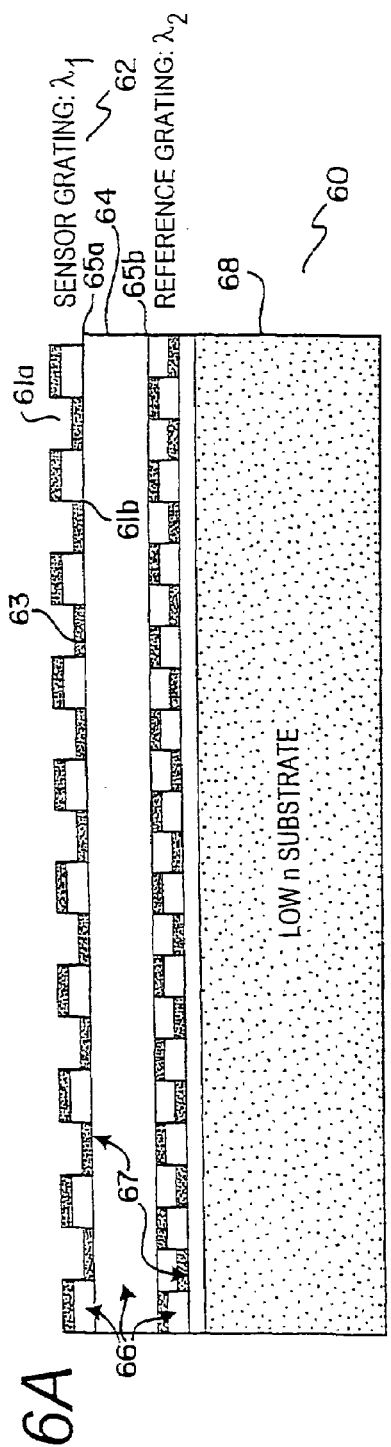
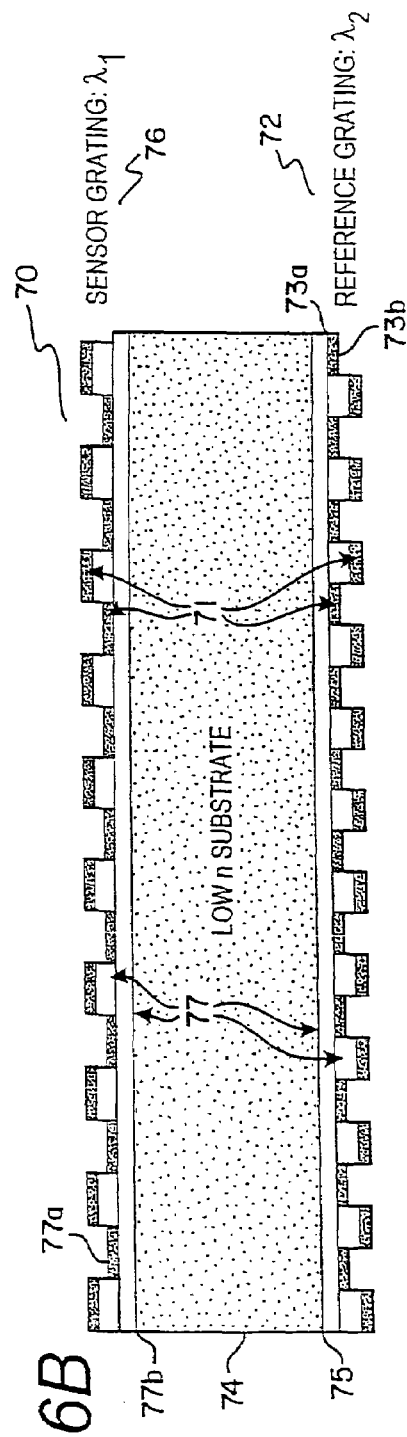
FIG. 6A
FIG. 6B
FIG. 6C

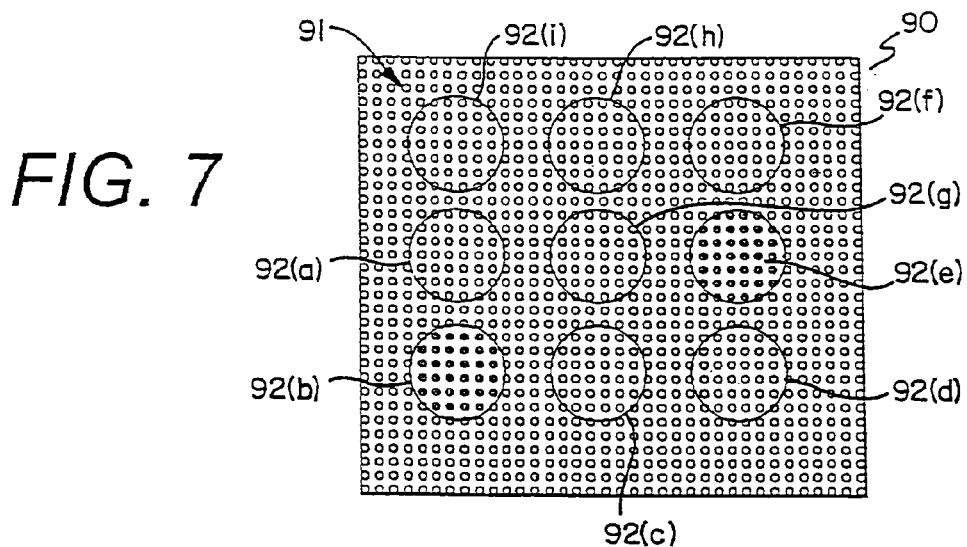
FIG. 7
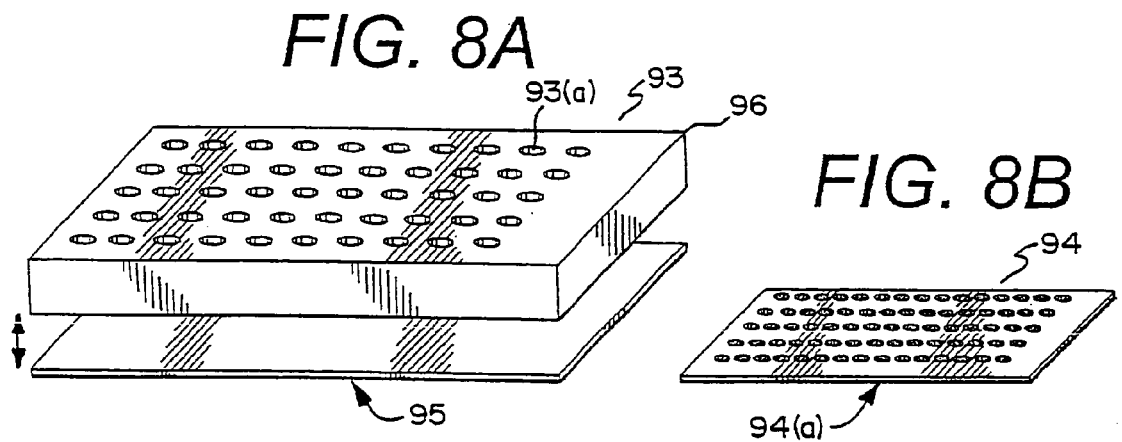
FIG. 8A
FIG. 8B
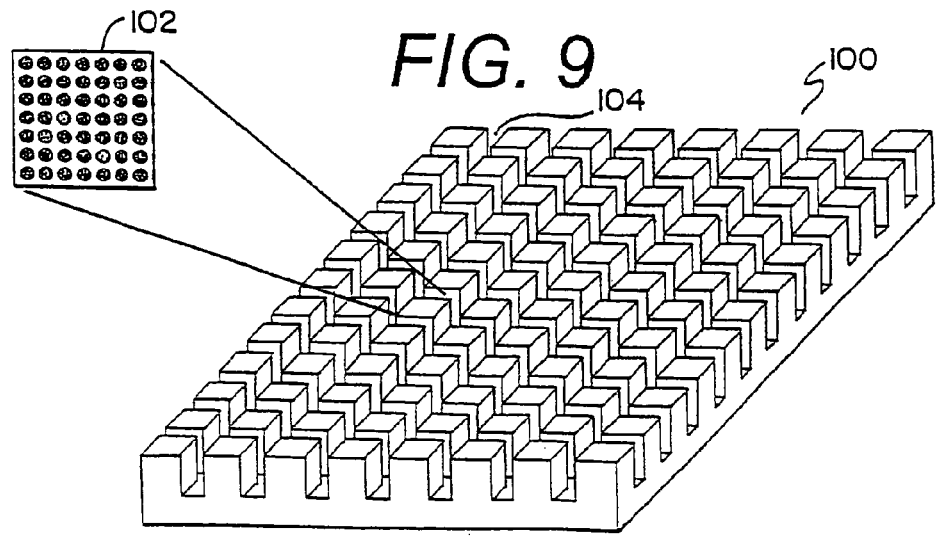
FIG. 9

SEPARATE ELECTRODE GRATING REGIONS — 117

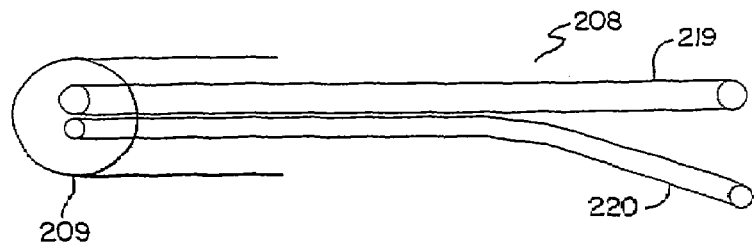
FIG. 18(a)
FIG. 18(b)
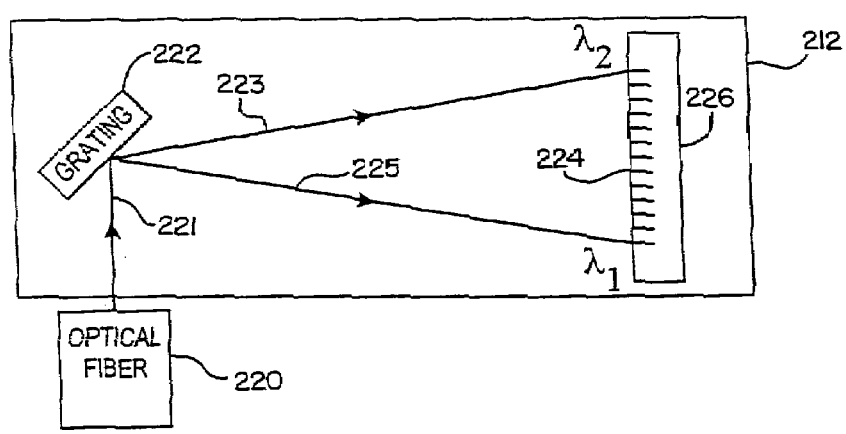
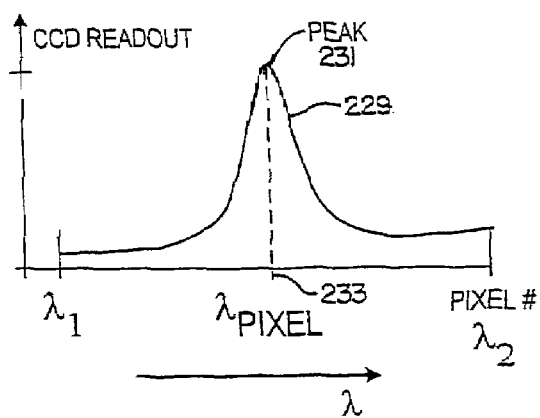
FIG. 18(c)

METHOD AND APPARATUS FOR DETECTING BIOMOLECULAR INTERACTIONS

A. PRIORITY

This application is a divisional of prior application Ser. No. 10/180,647 filed Jun. 26, 2002, now allowed, which is a continuation-in-part of U.S. patent application Ser. No. 09/930,352 filed Aug. 15, 2001, U.S. patent application Ser. No. 10/059,060 filed Jan. 28, 2002 now U.S. Pat. No. 7,070,987 and U.S. patent application Ser. No. 10/058,626 filed Jan. 28, 2002 now U.S. Pat. No. 6,951,715. U.S. application Ser. No. 09/930,352 filed Aug. 15, 2001 claims the benefit of U.S. provisional application 60/244,312 filed Oct. 30, 2000; U.S. provisional application 60/283,314 filed Apr. 12, 2001; and U.S. provisional application 60/303,028 filed Jul. 3, 2001. The content of the above-reference applications are herein entirely incorporated by reference and to which the reader is directed for further information.

B. TECHNICAL AREA OF THE INVENTION

The invention generally relates to methods, instrumentation and devices for detecting biomolecular interactions.

C. BACKGROUND OF THE INVENTION

With the completion of the sequencing of the human genome, one of the next grand challenges of molecular biology will be to understand how the many protein targets encoded by DNA interact with other proteins, small molecule pharmaceutical candidates, and a large host of enzymes and inhibitors. See e.g., Pandey & Mann, "Proteomics to study genes and genomes," *Nature*, 405, p. 837-846, 2000; Leigh Anderson et al., "Proteomics: applications in basic and applied biology," *Current Opinion in Biotechnology*, 11, p. 408-412, 2000; Patterson, "Proteomics: the industrialization of protein chemistry," *Current Opinion in Biotechnology*, 11, p. 413-418, 2000; MacBeath & Schreiber, "Printing Proteins as Microarrays for High-Throughput Function Determination," *Science*, 289, p. 1760-1763, 2000; De Wildt et al., "Antibody arrays for high-throughput screening of antibody-antigen interactions," *Nature Biotechnology*, 18, p. 989-994, 2000. To this end, tools that have the ability to simultaneously quantify many different biomolecular interactions with high sensitivity will find application in pharmaceutical discovery, proteomics, and diagnostics. Further, for these tools to find widespread use, they must be simple to use, inexpensive to own and operate, and applicable to a wide range of analytes that can include, for example, polynucleotides, peptides, small proteins, antibodies, and even entire cells.

Biosensors have been developed to detect a variety of biomolecular complexes including oligonucleotides, antibody-antigen interactions, hormone-receptor interactions, and enzyme-substrate interactions. In general, biosensors consist of two components: a highly specific recognition element and a transducer that converts the molecular recognition event into a quantifiable signal. Signal transduction has been accomplished by many methods, including fluorescence, interferometry (Jenison et al. "Interference-based detection of nucleic acid targets on optically coated silicon." *Nature Biotechnology*, 19, p. 62-65; Lin et al., "A porous silicon-based optical interferometric biosensor," *Science*, 278, p. 840-843, 1997), and gravimetry (A. Cunningham, Bioanalytical Sensors, John Wiley & Sons (1998)).

Of the optically-based transduction methods, direct methods that do not require labeling of analytes with fluorescent compounds are of interest due to the relative assay simplicity and ability to study the interaction of small molecules and proteins that are not readily labeled. Direct optical methods include surface plasmon resonance (SPR) (Jordan & Corn, "Surface Plasmon Resonance Imaging Measurements of Electrostatic Biopolymer Adsorption onto Chemically Modified Gold Surfaces," *Anal. Chem.*, 69:1449-1456 (1997), (grating couplers (Morhard et al., "Immobilization of antibodies in micropatterns for cell detection by optical diffraction," *Sensors and Actuators B*, 70, p. 232-242, 2000), ellipsometry (Jin et al., "A biosensor concept based on imaging ellipsometry for visualization of biomolecular interactions," *Analytical Biochemistry*, 232, p. 69-72, 1995), evanascent wave devices (Huber et al., "Direct optical immunosensing (sensitivity and selectivity)," *Sensors and Actuators B*, 6, p. 122-126, 1992), and reflectometry (Brecht & Gauglitz, "Optical probes and transducers," *Biosensors and Bioelectronics*, 10, p. 923-936, 1995). Theoretically predicted detection limits of these detection methods have been determined and experimentally confirmed to be feasible down to diagnostically relevant concentration ranges. However, to date, these methods have yet to yield commercially available high-throughput instruments that can perform high sensitivity assays without any type of label in a format that is readily compatible with the microtiter plate-based or microarray-based infrastructure that is most often used for high-throughput biomolecular interaction analysis. Therefore, there is a need in the art for compositions and methods that can achieve these goals.

D. SUMMARY OF THE INVENTION

It is an object of the invention to provide methods, instrumentation and devices for detecting binding of one or more specific binding substances to their respective binding partners. This and other objects of the invention are provided by one or more of the embodiments described below.

In one arrangement, an apparatus for detecting biochemical interactions occurring on a surface of a biosensor is provided. The apparatus comprises a light source. A first optical fiber is coupled to the light source and illuminates the biosensor. A second optical fiber detects a signal reflected from the surface of the biosensor. A spectrometer determines spectra of the reflected signal from the biosensor.

In an alternative arrangement, a biosensor imaging system comprises a light source generating white light. A collimator collimates the white light onto a surface of a biosensor. An imaging spectrometer receives reflected light from the biosensor. Software calculates a PWV of the reflected light.

In yet an alternative arrangement, an instrument for detecting light reflected from a surface of a biosensor comprises a light source and an illuminating fiber optically coupled to the light source and illuminates an area of the surface of the biosensor. A detecting fiber detects radiation reflected from the surface. A spectrometer receives the reflected radiation and software determines a peak wavelength value of the reflected wavelength In another arrangement, a method of measuring biochemical surface interactions of a biosensor is provided. The method includes the steps of incubating the biosensor at a predetermined temperature and providing a plurality of dual fiber optic probes. Other steps include providing each dual fiber optic probe with an illuminating fiber that is coupled to a light source. The illuminating fiber illuminating light towards a reflective surface of the biosensor. Each fiber is optically coupled to a separate light source and each dual fiber optic probe is provided with a detecting fiber that detects light reflected from the reflective surface. The detecting fiber is optically coupled to a spectrometer where the reflected light is processed.

Unlike surface plasmon resonance, resonant mirrors, and waveguide biosensors, the described compositions and methods enable many thousands of individual binding reactions to take place simultaneously upon the biosensor surface. This technology is useful in applications where large numbers of biomolecular interactions are measured in parallel, particularly when molecular labels alter or inhibit the functionality of the molecules under study. High-throughput screening of pharmaceutical compound libraries with protein targets, and microarray screening of protein-protein interactions for proteomics are examples of applications that require the sensitivity and throughput afforded by this approach. A biosensor of the invention can be manufactured, for example, in large areas using a plastic embossing process, and thus can be inexpensively incorporated into common disposable laboratory assay platforms such as microtiter plates and microarray slides.

These as well as other features and advantages of the present invention will become apparent to those of ordinary skill in the art by reading the following detailed description, with appropriate reference to the accompanying drawings.

E. BRIEF DESCRIPTION OF THE DRAWINGS

FIG. 6A illustrates a transparent resonant reflection superstructure arrangement.

FIG. 6B illustrates an alternative superstructure arrangement.

FIG. 6C illustrates a reflective surface of an alternative embodiment of a biosensor.

FIG. 7 illustrates an alternative embodiment of a biosensor grating structure.

FIG. 8A illustrates a biosensor embodiment incorporated into a microtiter plate.

FIG. 8B illustrates a microarray slide that may be utilized with the microtiter plate embodiment illustrated in FIG. 8A.

FIG. 9 illustrates an embodiment of a biosensor platform to perform assays.

FIG. 18(a) illustrates an optical fiber probe that may be utilized with the optical fiber probe measuring apparatus illustrated in FIG. 17.

FIG. 18(b) illustrates a general arrangement of a CCD chip and a spectrometer.

FIG. 18(c) illustrates a readout of a grating and the CCD chip illustrated in FIG. 18(b).

F. DETAILED DESCRIPTION OF THE INVENTION

1. Overview of Method and System

Figure 1A:
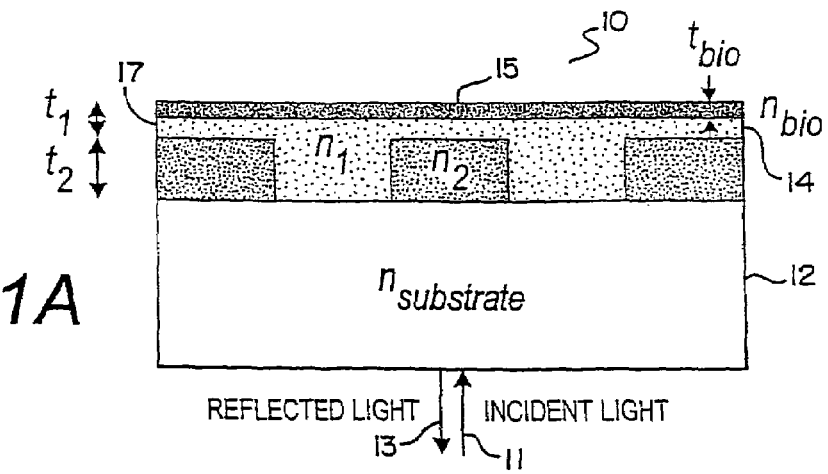
FIG. 1A illustrates a schematic diagram of an embodiment of an optical grating structure.

The present invention generally relates to a method and system for detecting biomolecular interactions. Preferably, these biomolecular interactions occur on a subwavelength structured surface biosensor, as described below.

One aspect of the present invention relates to a method and apparatus for detecting biochemical interactions occurring on a surface of a biosensor. In one embodiment, the biosensor is a colorimetric resonant optical biosensor embedded into a surface of a microarray slide, microtiter plate or other device.

The colorimetric resonant optical biosensor allows biochemical interactions to be measured on the sensor's surface without the use of fluorescent tags or colorimetric labels. The sensor surface contains an optical structure that, when illuminated with collimated white light, is designed to reflect only a narrow band of wavelengths. The narrow wavelength is described as a wavelength "peak." The "peak wavelength value" (PWV) changes when biological material is deposited or removed from the sensor surface.

A disclosed measurement instrument performs a number of functions, in addition to detection of a peak wavelength value. For example, the instrument can incubate a microtiter plate incorporating the biosensor plate at a user determined temperature. The instrument may also provide a mechanism for mixing samples within the microtiter plate wells while the microtiter plate resides within the instrument.

In one possible embodiment, the instrument illuminates the biosensor surface by directing a collimated white light on to the sensor structure. The illuminated light may take the form of a spot of collimated light. Alternatively, the light is generated in the form of a fan beam.

The instrument collects light reflected from the illuminated biosensor surface. The instrument may gather this reflected light from multiple locations on the biosensor surface simultaneously. The instrument can include a plurality of illumination probes that direct the light to a discrete number of positions across the biosensor surface. The instrument measures the Peak Wavelength Values (PWVs) of separate locations within the biosensor-embedded microtiter plate using a spectrometer. In one embodiment, the spectrometer is a single-point spectrometer. Alternatively, an imaging spectrometer is used.

The spectrometer produces a PWV image map of the sensor surface. In one embodiment, the measuring instrument spatially resolves PWV images with less than 200 micron resolution.

2. Subwavelength Structured Surface (SWS) Biosensor

In one embodiment of the present invention, a subwavelength structured surface (SWS) may be used to create a sharp optical resonant reflection at a particular wavelength that can be used to track with high sensitivity the interaction of biological materials, such as specific binding substances or binding partners or both. A colormetric resonant diffractive grating surface acts as a surface binding platform for specific binding substances.

Subwavelength structured surfaces are an unconventional type of diffractive optic that can mimic the effect of thin-film coatings. (Peng & Morris, "Resonant scattering from two-dimensional gratings," *J. Opt. Soc. Am. A*, Vol. 13, No. 5, p. 993, May; Magnusson, & Wang, "New principle for optical filters," *Appl. Phys. Lett.*, 61, No. 9, p. 1022, August, 1992; Peng & Morris, "Experimental demonstration of resonant anomalies in diffraction from two-dimensional gratings," *Optics Letters*, Vol. 21, No. 8, p. 549, April, 1996). A SWS structure contains a surface-relief, two-dimensional grating in which the grating period is small compared to the wavelength of incident light so that no diffractive orders other than the reflected and transmitted zeroth orders are allowed to propagate. A SWS surface narrowband filter can comprise a two-dimensional grating sandwiched between a substrate layer and a cover layer that fills the grating grooves. Optionally, a cover layer is not used. When the effective index of refraction of the grating region is greater than the substrate or the cover layer, a waveguide is created.

When a filter is designed according to one aspect of the present invention, incident light passes into the waveguide region. A two-dimensional grating structure selectively couples light at a narrow band of wavelengths into the waveguide. The light propagates only a short distance (on the order of 10-100 micrometers), undergoes scattering, and couples with the forward- and backward-propagating zeroth-order light. This sensitive coupling condition can produce a resonant grating effect on the reflected radiation spectrum, resulting in a narrow band of reflected or transmitted wavelengths. The depth and period of the two-dimensional grating are less than the wavelength of the resonant grating effect.

The reflected or transmitted color of this structure can be modulated by the addition of molecules such as specific binding substances or binding partners or both to the upper surface of the cover layer or the two-dimensional grating surface. The added molecules increase the optical path length of incident radiation through the structure, and thus modify the wavelength at which maximum reflectance or transmittance will occur.

In one embodiment, a biosensor, when illuminated with white light, is designed to reflect only a single wavelength. When specific binding substances are attached to the surface of the biosensor, the reflected wavelength (color) is shifted due to the change of the optical path of light that is coupled into the grating. By linking specific binding substances to a biosensor surface, complementary binding partner molecules can be detected without the use of any kind of fluorescent probe or particle label. The detection technique is capable of resolving changes of, for example, ~0.1 nm thickness of protein binding, and can be performed with the biosensor surface either immersed in fluid or dried. A more detailed description of these binding partners is provided in related and commonly assigned patent application Ser. No. 09/930,352, herein entirely incorporated by reference and to which the reader is directed for further information.

In one embodiment of the present invention, a detection system consists of, for example, a light source that illuminates a small spot of a biosensor at normal incidence through, for example, a fiber optic probe. A spectrometer collects the reflected light through, for example, a second fiber optic probe also at normal incidence. Because no physical contact occurs between the excitation/detection system and the biosensor surface, no special coupling prisms are required. The biosensor can, therefore, be adapted to a commonly used assay platform including, for example, microtiter plates and microarray slides. A spectrometer reading can be performed in several milliseconds, thus it is possible to efficiently measure a large number of molecular interactions taking place in parallel upon a biosensor surface, and to monitor reaction kinetics in real time.

This technology is useful in applications where large numbers of biomolecular interactions are measured in parallel, particularly when molecular labels would alter or inhibit the functionality of the molecules under study. High-throughput screening of pharmaceutical compound libraries with protein targets, and microarray screening of protein-protein interactions for proteomics are examples of applications that require the sensitivity and throughput afforded by the compositions and methods of the invention.

A schematic diagram of an example of a SWS structure 10 is shown in FIG. 1. In FIG. 1, $n_{substrate}$ represents a refractive index of a substrate material 12. $n_1$ represents the refractive index of an optional cover layer 14. $n_2$ represents the refractive index of a two-dimensional grating 16. $N_{bio}$ represents the refractive index of one or more specific binding substances 20. $t_1$ represents the thickness of the cover layer 14 above the two-dimensional grating structure 16. $t_2$ represents the thickness of the grating. $t_{bio}$ represents the thickness of the layer of one or more specific binding substances 20. In one embodiment, n2>n1 (see FIG. 1). Layer thicknesses (i.e. cover layer 14, one or more specific binding substances 20, or a two-dimensional grating 16) are selected to achieve resonant wavelength sensitivity to additional molecules on a top surface 15. A grating period is selected to achieve resonance at a desired wavelength.

Figure 1B:
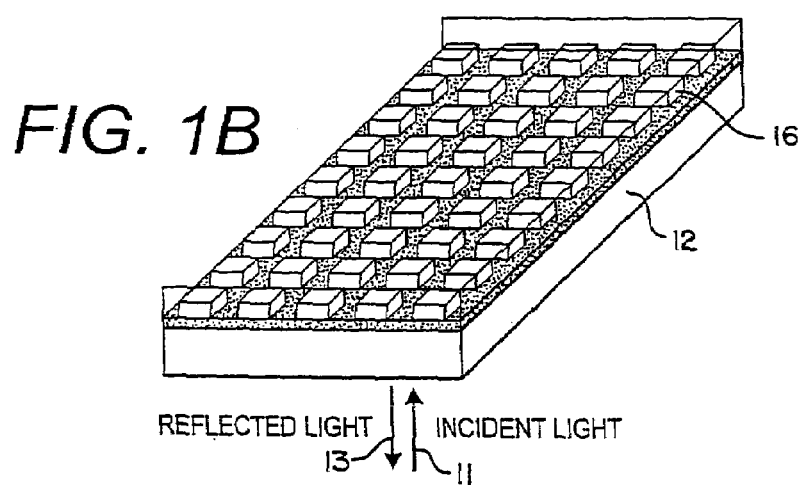
FIG. 1B illustrates a perspective view of the optical grating structure illustrated in FIG. 1A.

One embodiment provides a SWS biosensor, such as the SWS biosensor 10 illustrated in FIG. 1. The SWS biosensor 10 comprises a two-dimensional grating 16 and a substrate layer 12 that supports the two-dimensional grating 16. One or more specific binding substances 20 may be immobilized on a surface 15 of the two-dimensional grating 16 opposite of the substrate layer 12. Incident light 11 is polarized perpendicular to the grating structure and results in the reflected light 13. FIG. 1B illustrates a perspective view of the optical grating structure illustrated in FIG. 1A. Note that a SWS biosensor works equally well whether illumination and reflection occur from the top of the sensor surface or from the bottom, although FIG. 1 illustrates only the bottom illumination and reflection case.

The two-dimensional grating 16 can comprise a material, including, for example, zinc sulfide, titanium dioxide, tantalum oxide, and silicon nitride. A cross-sectional profile of a two-dimensional grating can comprise any periodically repeating function, for example, a "square-wave." The two-dimensional grating can comprise a repeating pattern of shapes selected from the group consisting of lines, squares, circles, ellipses, triangles, trapezoids, sinusoidal waves, ovals, rectangles, and hexagons. A sinusoidal cross-sectional profile is preferable for manufacturing applications that require embossing of a grating shape into a soft material such as plastic. In one embodiment of the biosensor, the depth of the grating is about 0.01 micron to about 1 micron and the period of the grating is about 0.01 micron to about 1 micron.

Figure 3A:
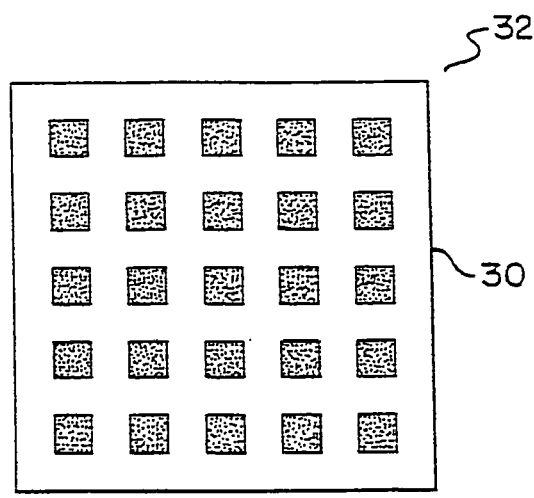
FIG. 3A illustrates a 2-D biosensor grating comprising a grid of squares/rectangles.
Figure 3B:
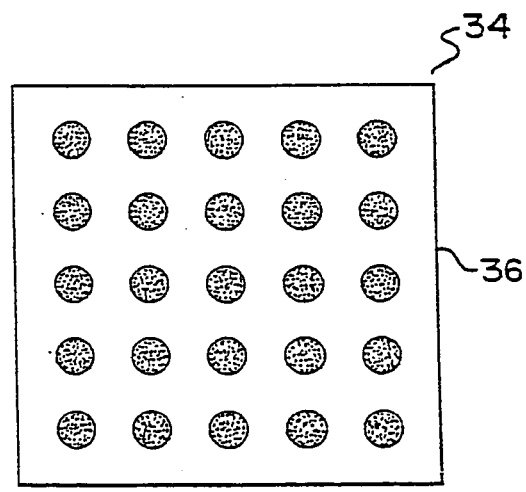
FIG. 3B illustrates a 2-D biosensor grating comprising a grid of circular holes.

Linear gratings have resonant characteristics where the illuminating light polarization is oriented perpendicular to the grating period. However, a hexagonal grid of holes has increased polarization symmetry over that of a rectangular grid of holes. Therefore, a calorimetric resonant reflection biosensor can comprise, for example, a hexagonal array of holes or alternatively, a grid of parallel lines. FIG. 3B illustrates a 2-D biosensor grating 34 including a grid of circular holes 36. FIG. 3A illustrates a 2-D biosensor grating 30 including a grid of squares/rectangles 32.

A linear grating has the same pitch (i.e. distance between regions of high and low refractive index), period, layer thicknesses, and material properties as the hexagonal array grating. However, light must be polarized perpendicular to the grating lines in order to be resonantly coupled into the optical structure. Therefore, a polarizing filter oriented with its polarization axis perpendicular to the linear grating is inserted between the illumination source and the biosensor surface. Because only a small portion of the illuminating light source is correctly polarized, a longer integration time is required to collect an equivalent amount of resonantly reflected light compared to a hexagonal grating.

While a linear grating can require either a higher intensity illumination source or a longer measurement integration time compared to a hexagonal grating, the fabrication requirements for the linear structure are generally less complex. A hexagonal grating pattern is produced by holographic exposure of photoresist to three mutually interfering laser beams. The three beams are aligned in order to produce a grating pattern that is essentially symmetrical in three directions. A linear grating pattern requires alignment of only two laser beams to produce a holographic exposure in photoresist, and therefore has a reduced alignment requirement. A linear grating pattern can also be produced by, for example, direct writing of photoresist with an electron beam. Also, several commercially available sources exist for producing linear grating "master" templates for embossing a grating structure into plastic.

Figure 2:
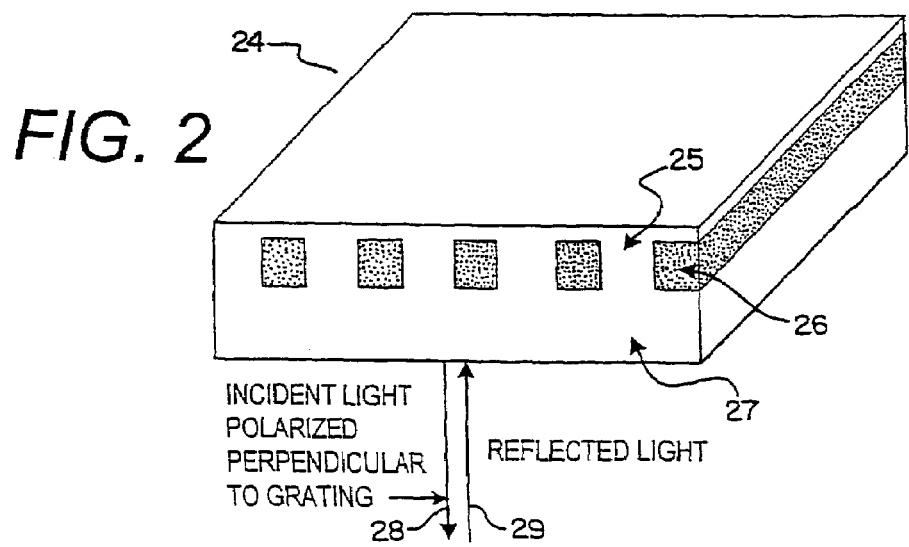
FIG. 2 illustrates a schematic drawing of a linear grating structure.

A schematic diagram of a linear grating structure 24 is shown in FIG. 2. The grating structure 24 includes a grating fill layer 25, a grating structural layer 26, and a substrate 27. Incident light 28 is polarized perpendicular to the grating structure and results in the reflected light 29.

A rectangular grid pattern can be produced in photoresist using an electron beam direct-write exposure system. A single wafer can be illuminated as a linear grating with two sequential exposures with the part rotated 90-degrees between exposures.

Figure 5A:
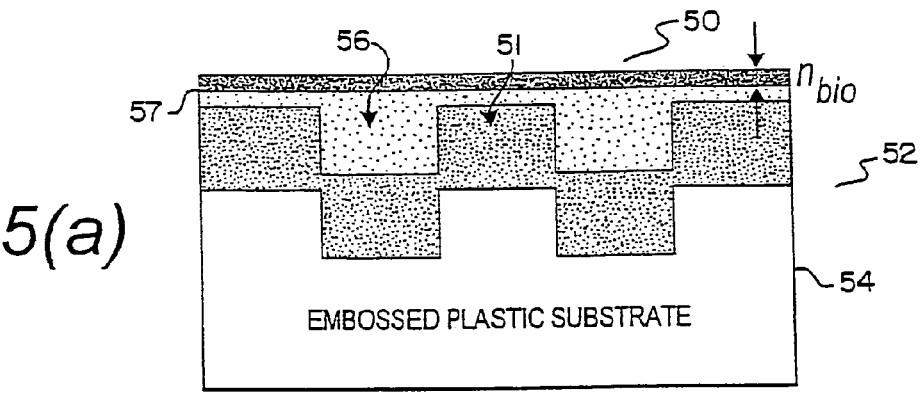
FIG. 5(a) illustrates an alternative embodiment of a biosensor utilizing an embossed substrate.

FIG. 5(a) illustrates a two-dimensional grating 50. Two-dimensional grating 50 comprises a "stepped" profile 52. In such a stepped profile 52, the profile has high refractive index regions of a single, fixed height embedded within a lower refractive index cover layer. The alternating regions of high and low refractive index provide an optical waveguide parallel to a top surface of the biosensor.

For manufacture, a stepped structure, such as the structure illustrated in FIG. 5(a), is etched or embossed into a substrate material 54 such as glass or plastic. A uniform thin film of higher refractive index material 51, such as silicon nitride (SiN) or zinc sulfide (ZnS) is deposited on this structure. The deposited layer follows the contour of the embossed or etched structure in the substrate 54. Consequently, the deposited material 51 has a surface relief profile that is essentially identical to the original embossed or etched profile of embossed plastic substrate 54.

The structure 50 can be completed with an application of an optional cover layer 56. Preferably, cover layer 56 includes a material having a lower refractive index than the higher refractive index material and has a substantially flat upper surface 57. The covering material 56 can be, for example, glass, epoxy, or plastic.

A stepped structure, such as the structure illustrated in FIG. 5(a), allows for reduced cost biosensor manufacturing, because the biosensor can be mass produced. For example, a "master" grating can be produced in glass, plastic, or metal using a three-beam laser holographic patterning process. See e.g., Cowan, The recording and large scale production of crossed holographic grating arrays using multiple beam interferometry, *Proc. Soc. Photo-optical Instum. Eng.* 503: 120 (1984). A master grating can be repeatedly used to emboss a plastic substrate. The embossed substrate 50 is subsequently coated with a high refractive index material and optionally, a cover layer 56.

Figure 4:
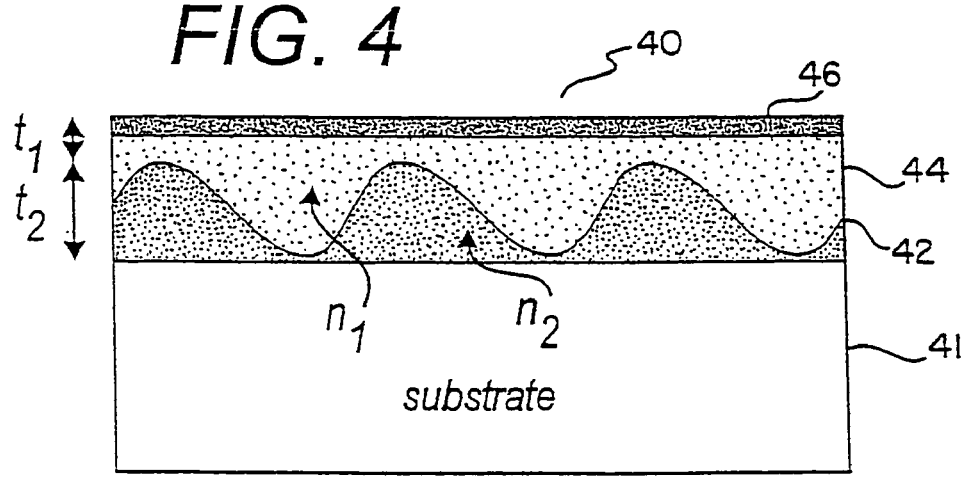
FIG. 4 illustrates an embodiment of a biosensor utilizing a sinusoidally varying grating profile.

While a stepped structure poses essentially few manufacturing complications, it is also possible to make a resonant biosensor in which a high refractive index material is not stepped. Rather, a biosensor could include a high refractive index material that varies with lateral position. For example, FIG. 4 illustrates an alternative embodiment of a biosensor 40. In this embodiment, the biosensor 40 includes a two-dimensional grating 42 having a high refractive index material varying with lateral position.

The biosensor 40 includes a substrate layer 41 that supports the two-dimensional grating 42. One or more specific binding substances 46 may be immobilized on a surface 43 of the two-dimensional grating opposite of the substrate layer 41. Sensor 40 includes a profile in which a high refractive index material of the two-dimensional grating 42, $n_2$, sinusoidally varies in height. This varying height of the two-dimensional grating 42 is represented by $t_2$.

To produce a resonant reflection at a particular wavelength, the period of the sinusoidally varying grating 42 is essentially identical to the period of an equivalent stepped structure. The resonant operation of the sinusoidally varying structure 40 and its functionality as a biosensor has been verified using GSOLVER (Grating Solver Development Company, Allen, Tex., USA) computer models.

Techniques for making two-dimensional gratings are disclosed in Wang, J. Opt. Soc. Am No. 8, August 1990, pp. 1529-44. Biosensors as herein described can be made in, for example, a semiconductor microfabrication facility. Biosensors can also be made on a plastic substrate using continuous embossing and optical coating processes. For this type of manufacturing process, a "master" structure is built in a rigid material such as glass or silicon. These "master" structures are used to generate "mother" structures in an epoxy or plastic using one of several types of replication procedures. The "mother" structure, in turn, is coated with a thin film of conductive material, and used as a mold to electroplate a thick film of nickel. The nickel "daughter" is released from the plastic "mother" structure. Finally, the nickel "daughter" is bonded to a cylindrical drum, which is used to continuously emboss the surface relief structure into a plastic film.

A device structure that uses an embossed plastic substrate is shown in FIG. 5(a). Following embossing, the plastic substrate 54 is overcoated with a thin film of high refractive index material 51. The substrate 54 may be optionally coated with a planarizing, cover layer polymer, and cut to appropriate size.

In one biosensor embodiment, a substrate for a SWS biosensor comprises glass, plastic or epoxy. Alternatively, a substrate and a two-dimensional grating comprises a single biosensor unit. That is, a two dimensional grating and substrate are formed from the same material, such as, for example, glass, plastic, or epoxy. The surface of a single unit comprising the two-dimensional grating is coated with a material having a high refractive index, for example, zinc sulfide, titanium dioxide, tantalum oxide, and silicon nitride. One or more specific binding substances can be immobilized on the surface of the material having a high refractive index or on an optional cover layer.

An alternative biosensor embodiment can further comprise a cover layer on the surface of a two-dimensional grating opposite of a substrate layer. Where a cover layer is present, the one or more specific binding substances are immobilized on the surface of the cover layer opposite of the two-dimensional grating. Preferably, a cover layer comprises a material that has a lower refractive index than a material that comprises the two-dimensional grating. A cover layer can be comprised of, for example, glass (including spin-on glass (SOG)), epoxy, or plastic.

Various polymers that meet the refractive index requirement of a biosensor can be used for a cover layer. For example, SOG can be used due to its favorable refractive index, ease of handling, and readiness of being activated with specific binding substances using a number of known glass surface activation techniques. When the flatness of the biosensor surface is not an issue for a particular application, a grating structure of SiN/glass can directly be used as the sensing surface, the activation of which can be done using the same means as on a glass surface.

Resonant reflection can also be obtained without a planarizing cover layer over a two-dimensional grating. For example, a biosensor can contain only a substrate coated with a structured thin film layer of high refractive index material. Without the use of a planarizing cover layer, the surrounding medium (such as air or water) fills the grating. Therefore, specific binding substances are immobilized to the biosensor on all surfaces a two-dimensional grating exposed to the specific binding substances, rather than only on an upper surface.

According to an alternative embodiment, a biosensor is illuminated with white light that contains light of every polarization angle. The orientation of the polarization angle with respect to repeating features in a biosensor grating determines a resonance wavelength. For example, a "linear grating" biosensor structure consisting of a set of repeating lines and spaces will have two optical polarizations that can generate separate resonant reflections. Light that is polarized perpendicularly to the lines is referred to as "s-polarized," whereas light that is polarized parallel to the lines is referred to as "p-polarized." Both the s and the p components of incident light exist simultaneously in an unfiltered illumination beam, and each component generates a separate resonant signal. A biosensor structure can generally be designed to optimize the properties of only one polarization (the s-polarization), and the non-optimized polarization can be removed by a polarizing filter.

Figure 5B:
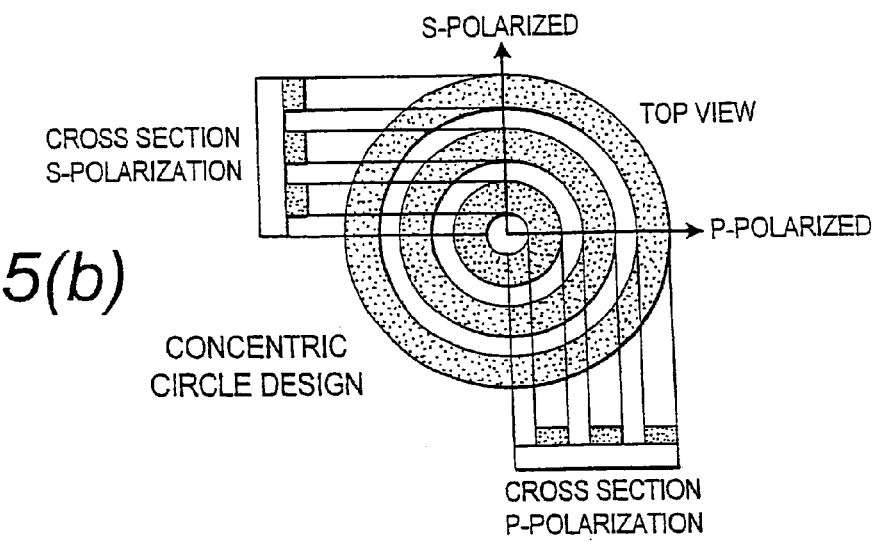
FIG. 5(b) illustrates an alternative embodiment of a biosensor utilizing a plurality of concentric rings.

In order to remove the polarization dependence, so that every polarization angle generates the same resonant reflection spectra, an alternate biosensor structure can be used. Such an alternative biosensor could consist of a plurality of concentric rings, such as the structure illustrated in FIG. 5(b). In this structure, the difference between an inside diameter and an outside diameter of each concentric ring is equal to about one-half of a grating period. Each successive ring has an inside diameter that is about one grating period greater than the inside diameter of the previous ring. The concentric ring pattern extends to cover a single sensor location—such as a microarray spot or a microtiter plate well. Each separate microarray spot or microtiter plate well has a separate concentric ring pattern centered within it.

All polarization directions of such a structure have the same cross-sectional profile. The concentric ring structure, such as the structure illustrated in FIG. 5(b), should be illuminated on-center to preserve polarization independence. The grating period of a concentric ring structure is preferably less than the wavelength of the resonantly reflected light. In one preferred embodiment, the grating period is about 0.01 micron to about 1 micron and the grating depth is about 0.01 to about 1 micron.

Figure 5C:
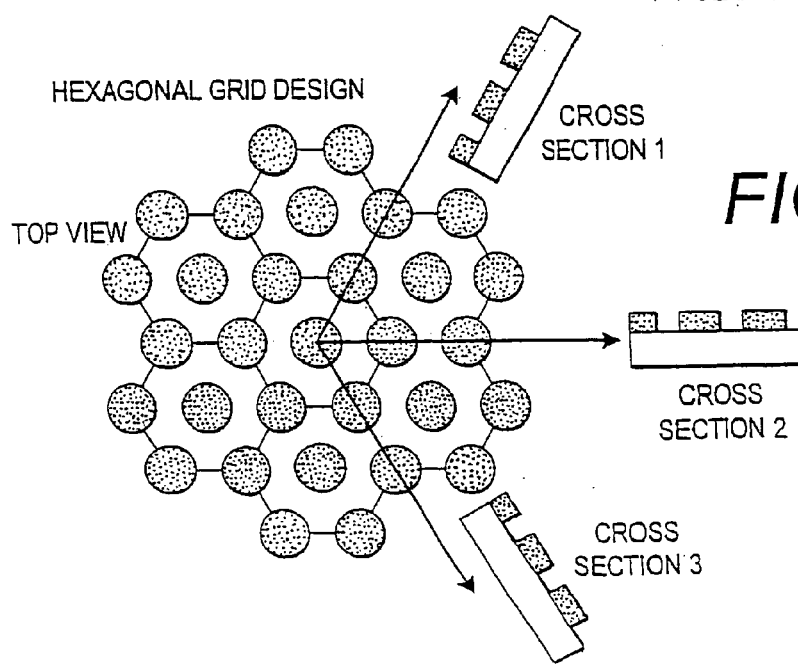
FIG. 5(c) illustrates an alternative embodiment of a biosensor having an array of closely packed hexagons.

In another biosensor embodiment, an array of holes or posts are provided on a sensor surface, such as the design illustrated in FIG. 5(c). Preferably, the array of holes or posts are arranged to approximate the concentric circle structure described above without requiring the illumination beam to be centered upon any particular location of the grid. Such an array pattern is automatically generated by the optical interference of three laser beams incident on a surface from three directions at equal angles. In this pattern, the holes (or posts) are centered upon the corners of an array of closely packed hexagons, as illustrated in FIG. 5(c). The holes or posts also occur in the center of each hexagon. Such a hexagonal grid of holes or posts has three polarization directions that "see" the same cross-sectional profile. The hexagonal grid structure, therefore, provides equivalent resonant reflection spectra using light of any polarization angle. Thus, no polarizing filter is required to remove unwanted reflected signal components. The period of the holes or posts can be about 0.01 microns to about 1 micron and the depth or height can be about 0.01 microns to about 1 micron. These and various other grid structures are disclosed and described in commonly assigned co-pending patent application Ser. No. 09/930,352 herein entirely incorporated by reference and to which the reader is directed for further details.

One possible detection apparatus and method provides for resonant reflection structures and transmission filter structures comprising concentric circle gratings and hexagonal grids of holes or posts. For a resonant reflection structure, light output is measured on the same side of the structure as the illuminating light beam. For example, as illustrated in FIG. 2, reflected light 29 is measured on the same side of the structure 21 as the illuminating light beam or incident light 28.

For a transmission filter structure, light output is measured on the opposite side of the structure as the illuminating beam. The reflected and transmitted signals are complementary. That is, if a wavelength is strongly reflected, it is weakly transmitted. Assuming no energy is absorbed in the structure itself, the combined reflected energy and transmitted energy at a given wavelength will remain a constant. The resonant reflection structure and transmission filters are designed to provide an efficient reflection at a specified wavelength. Therefore, a reflection filter will "pass" a narrow band of wavelengths, while a transmission filter will filter out or "cut" a narrow band of wavelengths from incident light.

A resonant reflection structure or a transmission filter structure can comprise a two-dimensional grating arranged in a pattern of concentric circles. (See, e.g., FIG. 5(b). A resonant reflection structure or transmission filter structure can also comprise a hexagonal grid of holes or posts. (See, e.g., FIG. 5(c)).

When these structures are illuminated with an illuminating light beam, a reflected radiation spectrum is produced. Such a radiation spectrum is independent of an illumination polarization angle of the illuminating light beam. A resonant grating effect is produced on the reflected radiation spectrum, wherein the depth and period of the two-dimensional grating or hexagonal grid of holes or posts are less than the wavelength of the resonant grating effect. These structures reflect a narrow band of light when the structure is illuminated with a broadband of light.

Resonant reflection structures and transmission filter structures of the invention can be used as biosensors. For example, one or more specific binding substances can be immobilized on the hexagonal grid of holes or posts or on the two-dimensional grating arranged in concentric circles.

In an alternative embodiment, a reference resonant signal is provided for more accurate measurement of peak resonant wavelength shifts. The reference resonant signal can cancel out environmental effects, including, for example, temperature or other types of unwanted noise. A reference signal can be provided using a resonant reflection superstructure that produces two separate resonant wavelengths. For example, FIG. 6A illustrates a transparent resonant reflection superstructure arrangement 60. Transparent resonant reflection superstructure 60 contains two sub-structures. The substructures comprise a low n cured polymer 66 and a high n dielectric 67. A first sub-structure comprises a first two-dimensional grating 62 with a top 61a and a bottom surface 61b. The top surface of a two-dimensional grating 61a comprises the grating surface 63. The first two-dimensional grating can comprise one or more specific binding substances immobilized on its top surface. The top surface of the first two-dimensional grating 63 will be in contact with a test sample (not shown). An optional substrate layer 64 may provide support to the bottom surface 61b of the first two-dimensional grating. The substrate layer 64 comprises a top 65a and bottom surface 65b. The top surface 65a of the substrate 64 is in contact with, and supports the bottom surface 61b of the first two-dimensional grating 62. A low n substrate 68 is also provided.

A second sub-structure 70, illustrated in FIG. 6B, comprises a second two-dimensional grating 72 with a top surface 73a and a bottom surface 73b. The second two-dimensional grating is not in contact with a test sample. The sub-structures comprise a low n cured polymer 77 and a high n dielectric 71. The second two-dimensional grating can be fabricated onto a bottom surface of the substrate 74 that supports a first two-dimensional grating 76. Where the second two-dimensional grating is fabricated on the substrate that supports the first two-dimensional grating, the bottom surface 73a of the second two-dimensional grating 72 can be fabricated onto the bottom surface 75 of the substrate 74. Therefore, the top surface 73b of the second two-dimensional grating 72 will face the opposite direction of a surface 77a of the first two-dimensional grating 76.

The top surface 73b of the second two-dimensional grating 72 can also be attached directly to the bottom surface of the first sub-structure. In this arrangement, the top surface of the second two-dimensional grating would face in the same direction as the top surface 77a of the first two-dimensional grating 76. A substrate 74 can support the bottom surface of the second two-dimensional grating in this arrangement.

Because the second sub-structure is not in physical contact with the test sample, its peak resonant wavelength is not subject to changes in the optical density of the test media, or deposition of specific binding substances or binding partners on the surface of the first two-dimensional grating. Therefore, such a superstructure produces two resonant signals. Because the location of the peak resonant wavelength in the second sub-structure is fixed, the difference in peak resonant wavelength between the two sub-structures provides a relative means for determining the amount of specific binding substances or binding partners or both deposited on the top surface of the first substructure that is exposed to the test sample.

A biosensor superstructure can be illuminated from its top surface or from its bottom surface, or from both surfaces. The peak resonance reflection wavelength of the first sub-structure is dependent on the optical density of material in contact with the superstructure surface. The peak resonance reflection wavelength of the second substructure is independent of the optical density of material in contact with the superstructure surface.

In an alternative embodiment, a biosensor is illuminated from a bottom surface. Approximately 50% of the incident light is reflected from the bottom surface of biosensor without reaching the active (or the top) surface of the biosensor. A thin film or physical structure can be included in a biosensor composition that is capable of maximizing the amount of light that is transmitted to the upper surface of the biosensor while minimizing the reflected energy at the resonant wavelength. The anti-reflection thin film or physical structure of the bottom surface of the biosensor can comprise, for example, a single dielectric thin film, or a stack of multiple dielectric thin films.

Alternatively, a "motheye" structure embossed into the bottom biosensor surface is provided. An example of a motheye structure is disclosed in Hobbs, et al. "Automated interference lithography system for generation of sub-micron feature size patterns," *Proc.* 1999 *Micromachine Technology for Diffracting and Holographic Optics, Society of Photo-Optical Instrumentation Engineers*, p. 124-135, (1999).

In one embodiment of the present invention, an interaction of a first molecule with a second test molecule is detected. A SWS biosensor as previously described is used. However, there are no specific binding substances immobilized on a SWS biosensor. Therefore, the biosensor comprises a two-dimensional grating, a substrate layer that supports the two-dimensional grating. Optionally, a cover layer may be provided. As described above, when the biosensor is illuminated a resonant grating effect is produced on the reflected radiation spectrum, and the depth and period of the two-dimensional grating are less than the wavelength of the resonant grating effect.

To detect an interaction of a first molecule with a second test molecule, a mixture of the first and second molecules is applied to a distinct location on a biosensor. Such a location may be one area, spot, or one well on the biosensor. Alternatively, it could be a large area on the biosensor. A mixture of the first molecule with a third control molecule is also applied to a distinct location on a biosensor. The biosensor can be the same biosensor as described above, or can be a second biosensor. If the biosensor is the same biosensor, a second distinct location can be used for the mixture of the first molecule and the third control molecule.

Alternatively, the same distinct biosensor location can be used after the first and second molecules are washed from the biosensor. The third control molecule does not interact with the first molecule and may be about the same size as the first molecule. A shift in the reflected wavelength of light from the distinct locations of the biosensor or biosensors is measured using a read out method and apparatus as detailed below.

If the shift in the reflected wavelength of light from the distinct location having the first molecule and the second test molecule is greater than the shift in the reflected wavelength from the distinct location having the first molecule and the third control molecule, then the first molecule and the second test molecule interact. Interaction can be, for example, hybridization of nucleic acid molecules, specific binding of an antibody or antibody fragment to an antigen, and binding of polypeptides. A first molecule, second test molecule, or third control molecule can be, for example, a nucleic acid, polypeptide, antigen, polyclonal antibody, monoclonal antibody, single chain antibody (scFv), F(ab) fragment, F(ab')$_2$ fragment, Fv fragment, small organic molecule, cell, virus, and bacteria 3. Specific Binding Substances and Binding Partners One or more specific binding substances may be immobilized on the two-dimensional grating or cover layer, if present. Immobilization may occur by physical adsorption or by chemical binding. A specific binding substance can be, for example, a nucleic acid, polypeptide, antigen, polyclonal antibody, monoclonal antibody, single chain antibody (scFv), F(ab) fragment, F(ab')$_2$ fragment, Fv fragment, small organic molecule, cell, virus, bacteria, or biological sample. A biological sample can be for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatitc fluid.

Preferably, one or more specific binding substances are arranged in a microarray of distinct locations on a biosensor. A microarray of specific binding substances comprises one or more specific binding substances on a surface of a biosensor such that a biosensor surface contains a plurality of distinct locations, each with a different specific binding substance or with a different amount of a specific binding substance. For example, an array can comprise 1, 10, 100, 1,000, 10,000, or 100,000 distinct locations. A biosensor surface with a large number of distinct locations is called a microarray because one or more specific binding substances are typically laid out in a regular grid pattern in x-y coordinates. However, a microarray can comprise one or more specific binding substances laid out in a regular or irregular pattern. For example, distinct locations can define a microarray of spots of one or more specific binding substances.

A microarray spot can range from about 50 to about 500 microns in diameter. Alternatively, a microarray spot can range from about 150 to about 200 microns in diameter. One or more specific binding substances can be bound to their specific binding partners.

In one biosensor embodiment, a microarray on a biosensor is created by placing microdroplets of one or more specific binding substances onto, for example, an x-y grid of locations on a two-dimensional grating or cover layer surface. When the biosensor is exposed to a test sample comprising one or more binding partners, the binding partners will be preferentially attracted to distinct locations on the microarray that comprise specific binding substances that have high affinity for the binding partners. Some of the distinct locations will gather binding partners onto their surface, while other locations will not.

A specific binding substance specifically binds to a binding partner that is added to the surface of a biosensor of the invention. A specific binding substance specifically binds to its binding partner, but does not substantially bind other binding partners added to the surface of a biosensor. For example, where the specific binding substance is an antibody and its binding partner is a particular antigen, the antibody specifically binds to the particular antigen, but does not substantially bind other antigens. A binding partner can be, for example, a nucleic acid, polypeptide, antigen, polyclonal antibody, monoclonal antibody, single chain antibody (scFv), F(ab) fragment, F(ab')$_2$ fragment, Fv fragment, small organic molecule, cell, virus, bacteria, and biological sample. A biological sample can be, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, and prostatitc fluid.

In an alternative embodiment, a nucleic acid microarray is provided, in which each distinct location within the array contains a different nucleic acid molecule. In this embodiment, the spots within the nucleic acid microarray detect complementary chemical binding with an opposing strand of a nucleic acid in a test sample.

While microtiter plates are a common format used for biochemical assays, microarrays are increasingly seen as a means for increasing the number of biochemical interactions that can be measured at one time while minimizing the volume of precious reagents. By application of specific binding substances with a microarray spotter onto a biosensor of the invention, specific binding substance densities of 10,000 specific binding substances/in$^2$ can be obtained. By focusing an illumination beam of a fiber optic probe to interrogate a single microarray location, a biosensor can be used as a label-free microarray readout system.

4. Immobilization of One or More Specific Binding Substances

Immobilization of one or more binding substances onto a biosensor is performed so that a specific binding substance will not be washed away by rinsing procedures, and so that its binding to binding partners in a test sample is unimpeded by the biosensor surface. Several different types of surface chemistry strategies have been implemented for covalent attachment of specific binding substances to, for example, glass for use in various types of microarrays and biosensors. These methods can be adapted to a biosensor embodiment. Surface preparation of a biosensor so that it contains certain required functional groups for binding one or more specific binding substances can be an integral part of the biosensor manufacturing process.

One or more specific binding substances can be attached to a biosensor surface by physical adsorption (i.e., without the use of chemical linkers). Alternatively, one or more specific binding substances can be attached to a biosensor surface by chemical binding (i.e., with the use of chemical linkers). Chemical binding can generate stronger attachment of specific binding substances on a biosensor surface. Chemical binding also provides defined orientation and conformation of the surface-bound molecules. Several examples of chemical binding of specific binding substances to a biosensor embodying one aspect of the invention are described in detail in related commonly assigned co-pending patent application Ser. No. 09/930,352 herein entirely incorporated by reference and to which the reader is directed for further detail.

Other types of chemical binding include, for example, amine activation, aldehyde activation, and nickel activation. These surfaces can be used to attach several different types of chemical linkers to a biosensor surface. While an amine surface can be used to attach several types of linker molecules, an aldehyde surface can be used to bind proteins directly, without an additional linker. A nickel surface can be used to bind molecules that have an incorporated histidine ("his") tag. Detection of "his-tagged" molecules with a nickel-activated surface is well known in the art (Whitesides, *Anal. Chem.* 68, 490, (1996)).

Immobilization of specific binding substances to plastic, epoxy, or high refractive index material can be performed essentially as described for immobilization to glass. However, an acid wash step may be eliminated where such a treatment would damage the material to which the specific binding substances are immobilized.

For the detection of binding partners at concentrations of less than about ~0.1 ng/ml, one may amplify and transduce binding partners bound to a biosensor into an additional layer on the biosensor surface. The increased mass deposited on the biosensor can be detected as a consequence of increased optical path length. By incorporating greater mass onto a biosensor surface, an optical density of binding partners on the surface is also increased, thus rendering a greater resonant wavelength shift than would occur without the added mass. The addition of mass can be accomplished, for example, enzymatically, through a "sandwich" assay, or by direct application of mass to the biosensor surface in the form of appropriately conjugated beads or polymers of various size and composition. This principle has been exploited for other types of optical biosensors to demonstrate sensitivity increases over 1500× beyond sensitivity limits achieved without mass amplification. See, e.g., Jenison et al., "Interference-based detection of nucleic acid targets on optically coated silicon," *Nature Biotechnology,* 19: 62-65, 2001.

5. Surface-Relief Volume Diffractive Biosensors

In an alternative embodiment, a biosensor comprises volume surface-relief volume diffractive structures (a SRVD biosensor). SRVD biosensors have a surface that reflects predominantly at a particular narrow band of optical wavelengths when illuminated with a broad band of optical wavelengths. Where specific binding substances and/or binding partners are immobilized on a SRVD biosensor, the reflected wavelength of light is shifted. One-dimensional surfaces, such as thin film interference filters and Bragg reflectors, can select a narrow range of reflected or transmitted wavelengths from a broadband excitation source. However, the deposition of additional material, such as specific binding substances and/or binding partners onto their upper surface results only in a change in the resonance linewidth, rather than the resonance wavelength. In contrast, SRVD biosensors have the ability to alter the reflected wavelength with the addition of material, such as specific binding substances and/or binding partners to the surface.

A SRVD biosensor comprises a sheet material having a first and second surface. The first surface of the sheet material defines relief volume diffraction structures. Sheet material can comprise, for example, plastic, glass, semiconductor wafer, or metal film.

A relief volume diffractive structure can be, for example, a two-dimensional grating, as described above, or a three-dimensional surface-relief volume diffractive grating. The depth and period of relief volume diffraction structures are less than the resonance wavelength of light reflected from a biosensor.

A three-dimensional surface-relief volume diffractive grating can be, for example, a three-dimensional phase-quantized terraced surface relief pattern whose groove pattern resembles a stepped pyramid. When such a grating is illuminated by a beam of broadband radiation, light will be coherently reflected from the equally spaced terraces at a wavelength given by twice the step spacing times the index of refraction of the surrounding medium. Light of a given wavelength is resonantly diffracted or reflected from the steps that are a half-wavelength apart, and with a bandwidth that is inversely proportional to the number of steps. The reflected or diffracted color can be controlled by the deposition of a dielectric layer so that a new wavelength is selected, depending on the index of refraction of the coating.

A stepped-phase structure can be produced first in photoresist by coherently exposing a thin photoresist film to three laser beams, as described previously. See e.g., Cowen, "The recording and large scale replication of crossed holographic grating arrays using multiple beam interferometry," in *International Conference on the Application, Theory, and Fabrication of Periodic Structures, Diffraction Gratings, and Moire Phenomena II*, Lerner, ed., Proc. Soc. Photo-Opt. Instrum. Eng., 503, 120-129, 1984; Cowen, "Holographic honeycomb microlens," *Opt. Eng.* 24, 796-802 (1985); Cowen & Slafer, "The recording and replication of holographic micropatterns for the ordering of photographic emulsion grains in film systems," *J. Imaging Sci.* 31, 100-107, 1987. The nonlinear etching characteristics of photoresist are used to develop the exposed film to create a three-dimensional relief pattern. The photoresist structure is then replicated using standard embossing procedures. For example, a thin silver film may be deposited over the photoresist structure to form a conducting layer upon which a thick film of nickel can be electroplated. The nickel "master" plate is then used to emboss directly into a plastic film, such as vinyl, that has been softened by heating or solvent.

A theory describing the design and fabrication of three-dimensional phase-quantized terraced surface relief pattern that resemble stepped pyramids is described: Cowen, "Aztec surface-relief volume diffractive structure," *J. Opt. Soc. Am. A*, 7:1529 (1990).

An example of a three-dimensional phase-quantized terraced surface relief pattern may be a pattern that resembles a stepped pyramid. Each inverted pyramid is approximately 1 micron in diameter. Preferably, each inverted pyramid can be about 0.5 to about 5 microns diameter, including for example, about 1 micron. The pyramid structures can be close-packed so that a typical microarray spot with a diameter of 150-200 microns can incorporate several hundred stepped pyramid structures. The relief volume diffraction structures have a period of about 0.1 to about 1 micron and a depth of about 0.1 to about 1 micron.

FIG. 6 illustrates a reflective surface 82 of a biosensor 80. The reflective surface 82 includes a first microarray spot 84 and a second microarray spot 86. The first microarray spot 82 is not provided with an adsorbed material while the second microarray spot 84 is provided with an adsorbed protein. Consequently, the index or refraction for the first spot remains unchanged, i.e., $n_{air}$=1. The index of refraction for the second spot will change to that of an absorbed protein, i.e., $n_{protein}$=1.4.

As white light 81 is illuminated onto the first microarray spot 84, blue light 89 will be reflected. Alternatively, the reflected light of white light 88 illuminated unto the second microarray spot 86 will be different (i.e., green light 87) because of the different index of refraction.

FIG. 6 demonstrates how individual microarray locations (with an entire microarray spot incorporating hundreds of pyramids now represented by a single pyramid for one microarray spot) can be optically queried to determine if specific binding substances or binding partners are adsorbed onto the surface. When the structure is illuminated with white light, structures without significant bound material will reflect wavelengths determined by the step height of the structure. When higher refractive index material, such as binding partners or specific binding substances, are incorporated over the reflective metal surface, the reflected wavelength is modified to shift toward longer wavelengths. The color that is reflected from the terraced step structure is theoretically given as twice the step height times the index of refraction of a reflective material that is coated onto the first surface of a sheet material of a SRVD biosensor. A reflective material can be, for example silver, aluminum, or gold.

One or more specific binding substances, as described above, are immobilized on the reflective material of a SRVD biosensor. One or more specific binding substances can be arranged in microarray of distinct locations, as described above, on the reflective material. FIG. 7 illustrates an embodiment of a microarray sensor 90. In this embodiment, the microarray biosensor 90 comprises a 9-element microarray biosensor. A plurality of individual grating structures, represented in FIG. 7 by small circles, such as small circle 91, lie within each microarray spot. The microarray spots, represented by the larger circles 92(a-i), reflect white light at a specific wavelength. This specific wavelength is determined by the refractive index of material on the microarray surface. Microarray locations with additional adsorbed material will have reflected wavelengths that are shifted toward longer wavelengths, represented by the larger circles.

Because the reflected wavelength of light from a SRVD biosensor is confined to a narrow bandwidth, very small changes in the optical characteristics of the surface manifest themselves in easily observed changes in reflected wavelength spectra. The narrow reflection bandwidth provides a surface adsorption sensitivity advantage compared to reflectance spectrometry on a flat surface.

A SRVD biosensor reflects light predominantly at a first single optical wavelength when illuminated with a broad band of optical wavelengths, and reflects light at a second single optical wavelength when one or more specific binding substances are immobilized on the reflective surface. The reflection at the second optical wavelength results from optical interference. A SRVD biosensor also reflects light at a third single optical wavelength when the one or more specific binding substances are bound to their respective binding partners, due to optical interference.

Readout of the reflected color can be performed serially by focusing a microscope objective onto individual microarray spots and reading the reflected spectrum with the aid of a spectrograph or imaging spectrometer, or in parallel by, for example, projecting the reflected image of the microarray onto an imaging spectrometer incorporating a high resolution color CCD camera.

A SRVD biosensor can be manufactured by, for example, producing a metal master plate, and stamping a relief volume diffractive structure into, for example, a plastic material like vinyl. After stamping, the surface is made reflective by blanket deposition of, for example, a thin metal film such as gold, silver, or aluminum. Compared to MEMS-based biosensors that rely upon photolithography, etching, and wafer bonding procedures, the manufacture of a SRVD biosensor is very inexpensive.

6. Liquid-Containing Vessels

A SWS or SRVD biosensor embodiment can comprise an inner surface. In one preferred embodiment, such an inner surface is a bottom surface of a liquid-containing vessel. A liquid-containing vessel can be, for example, a microtiter plate well, a test tube, a petri dish, or a microfluidic channel. In one embodiment, a SWS or SRVD biosensor is incorporated into a microtiter plate.

For example, a SWS biosensor or SRVD biosensor can be incorporated into the bottom surface of a microtiter plate by assembling the walls of the reaction vessels over the resonant reflection surface, so that each reaction "spot" can be exposed to a distinct test sample. Therefore, each individual microtiter plate well can act as a separate reaction vessel. Separate chemical reactions can, therefore, occur within adjacent wells without intermixing reaction fluids and chemically distinct test solutions can be applied to individual wells.

Several methods for attaching a biosensor of the invention to the bottom surface of bottomless microtiter plates can be used, including, for example, adhesive attachment, ultrasonic welding, and laser welding.

The most common assay formats for pharmaceutical screening laboratories, molecular biology research laboratories, and diagnostic assay laboratories are microtiter plates. The plates are standard-sized plastic cartridges that can contain 96, 384, or 1536 individual reaction vessels arranged in a grid. Due to the standard mechanical configuration of these plates, liquid dispensing, robotic plate handling, and detection systems are designed to work with this common format. A biosensor incorporating an embodiment of the present invention can be incorporated into the bottom surface of a standard microtiter plate. See, e.g., FIGS. 8A & 8B.

For example, FIG. 8A illustrates a microtiter plate 93. The microtiter plate 93 is a bottomless microtiter plate having a plurality of holes 93(a). The plurality of holes, preferably arranged in an array, extend from a top surface 96 to a bottom surface 95 of the microtiter plate 93. A microarray slide 94 (FIG. 8B) is provided along the plate bottom surface 95. The slide acts as a resonant reflection biosensor surface due to the incorporation of structure in the bottom surface in accordance with FIG. 4 or 5, described previously.

Because the biosensor surface can be fabricated in large areas, and because a readout system incorporating one aspect of the present invention does not make physical contact with the biosensor surface, a plurality of individual biosensor areas can be defined.

7. Holding Fixtures

A number of biosensors that are, for example, about 1 mm² to about 5 mm², and preferably less than about 3×3 mm² can be arranged onto a holding fixture that can simultaneously dip the biosensors into separate liquid-containing vessels, such as wells of a microtiter plate, for example, a 96-, 384-, or 1536-well microtiter plate. Other types of liquid containing vessels could also be used including a micro fluidic device, a microarray chip, a petri dish, a microscope slide, and a flask.

FIG. 9 illustrates an embodiment of a holding fixture 100. Fixture 100 includes a plurality of wells 104. In this embodiment, the fixture includes 96 wells arranged in an array comprising 8 rows and 12 columns. Each well 104 includes a plurality of microtiter plate spots 102. Where, for example, the biosensor includes 96 wells, a total of 4800 plate spots are provided. (4800=96×50). Therefore, with the embodiment illustrated in FIG. 9, this holding fixture 100 could be dipped into a 96-well plate and perform 4800 assays.

Each of the biosensors can contain multiple distinct locations. A holding fixture has one or more attached biosensors so that each individual biosensor can be lowered into a separate, liquid-containing vessel. A holding fixture can comprise plastic, epoxy or metal. For example, 50, 96, 384, or 1,000, or 1,536 biosensors can be arranged on a holding fixture, where each biosensor has 25, 100, 500, or 1,000 distinct locations. As an example, where 96 biosensors are attached to a holding fixture and each biosensor comprises 100 distinct locations, 9600 biochemical assays can be simultaneously performed.

8. Methods of Using SWS and SRVD Biosensors

The disclosed SWS and SRVD biosensors can be used to study one or a number of specific binding substance/binding partner interactions in parallel. Binding of one or more specific binding substances to their respective binding partners can be detected, without the use of labels. Detection occurs by applying one or more binding partners to a SWS or SRVD biosensor that have one or more specific binding substances immobilized on their surfaces. A SWS biosensor is illuminated with light and a maxima in reflected wavelength, alternatively or a minima in transmitted wavelength is detected from the biosensor. If one or more specific binding substances have bound to their respective binding partners, then the reflected wavelength of light is shifted as compared to a situation where one or more specific binding substances have not bound to their respective binding partners. The shift is detected by a spectrographic device as described in further detail. Where a SWS biosensor is coated with an array of distinct locations containing the one or more specific binding substances, then a maxima in reflected wavelength or minima in transmitted wavelength of light is detected from each distinct location of the biosensor.

A SRVD biosensor is illuminated with light after binding partners have been added and the reflected wavelength of light is detected from the biosensor. Where one or more specific binding substances have bound to their respective binding partners, the reflected wavelength of light is shifted.

In an alternative embodiment, a variety of specific binding substances, for example, antibodies, can be immobilized in an array format onto a biosensor of the invention. The biosensor is contacted with a test sample of interest comprising binding partners, such as proteins. Only the proteins that specifically bind to the antibodies immobilized on the biosensor remain bound to the biosensor. Such an approach is essentially a large-scale version of an enzyme-linked immunosorbent assay. However, in this embodiment, the use of an enzyme or fluorescent label is not required.

The activity of an enzyme can be detected by applying one or more enzymes to a SWS or SRVD biosensor to which one or more specific binding substances have been immobilized. The biosensor is washed and illuminated with light. The reflected wavelength of light is detected from the biosensor. Where the one or more enzymes have altered the one or more specific binding substances of the biosensor by enzymatic activity, the reflected wavelength of light is shifted.

Additionally, a test sample, for example, cell lysates containing binding partners can be applied to a biosensor of the invention, followed by washing to remove unbound material. The binding partners that bind to a biosensor can be eluted from the biosensor and identified by, for example, mass spectrometry. Optionally, a phage DNA display library can be applied to a biosensor of the invention followed by washing to remove unbound material. Individual phage particles bound to the biosensor can be isolated and the inserts in these phage particles can then be sequenced to determine the identity of the binding partner.

For the above applications, and in particular proteomics applications, the ability to selectively bind material, such as binding partners from a test sample onto a preferred biosensor, followed by the ability to selectively remove bound material from a distinct location of the biosensor for further analysis is advantageous. Biosensors may also be capable of detecting and quantifying the amount of a binding partner from a sample that is bound to a biosensor array distinct location by measuring the shift in reflected wavelength of light. For example, the wavelength shift at one distinct biosensor location can be compared to positive and negative controls at other distinct biosensor locations to determine the amount of a binding partner that is bound to a biosensor array distinct location.

9. SWS and Electrically Conducting Material

An alternative biosensor embodiment structure is provided that enables a biosensor array to selectively attract or repel binding partners from individual distinct locations on a biosensor. As is well known in the art, an electromotive force can be applied to biological molecules such as nucleic acids and amino acids subjecting them to an electric field. Because these molecules are electronegative, they are attracted to a positively charged electrode and repelled by a negatively charged electrode.

In one embodiment of the present invention, a grating structure of a resonant optical biosensor is provided with an electrically conducting material rather than an electrically insulating material. An electric field is applied near the biosensor surface. Where a grating operates as both a resonant reflector biosensor and as an electrode, the grating comprises a material that is both optically transparent near the resonant wavelength, and also has low resistivity. In one biosensor embodiment, the material is indium tin oxide, $InSn_xO_{1-x}$(ITO). ITO is commonly used to produce transparent electrodes for flat panel optical displays, and is therefore readily available at low cost on large glass sheets. The refractive index of ITO can be adjusted by controlling x, the fraction of Sn that is present in the material. Because the liquid test sample solution has mobile ions (and will therefore be an electrical conductor), the ITO electrodes are coated with an insulating material. In a preferred resonant optical biosensor embodiment, a grating layer is coated with a layer with lower refractive index material. Materials such as cured photoresist (n=1.65), cured optical epoxy (n=1.5), and glass (n=1.4-1.5) are strong electrical insulators that also have a refractive index that is lower than ITO (n=2.0-2.65). A cross-sectional diagram of a biosensor that incorporates an ITO grating is shown in FIG. 16.

Figure 16:
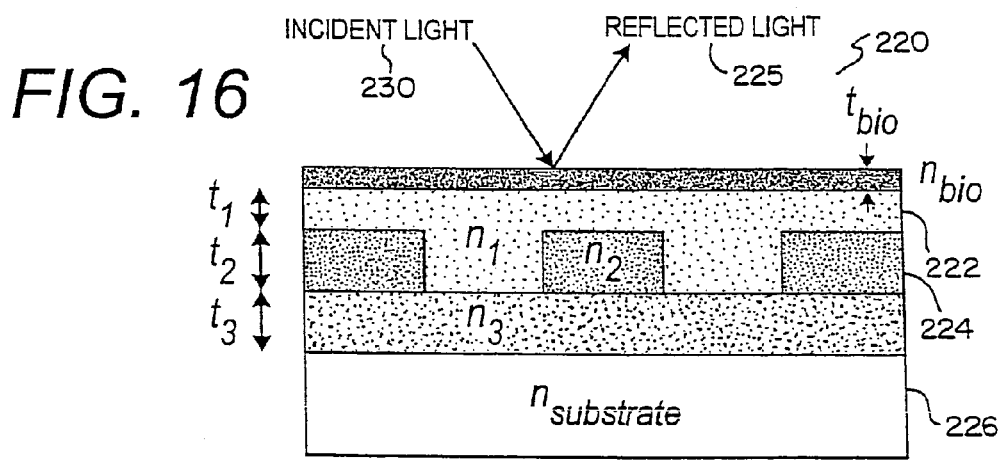
FIG. 16 illustrates an embodiment of a biosensor incorporating an ITO grating.

As illustrated in FIG. 16, $n_1$ represents the refractive index of an electrical insulator 222. $n_2$ represents the refractive index of a two-dimensional grating 224. $t_1$ represents the thickness of the electrical insulator 222. $t_2$ represents the thickness of the two-dimensional grating 224. $n_{bio}$ represents the refractive index of one or more specific binding substances 228 and $t_{BIO}$ represents the thickness of the one or more specific binding substances 228.

A grating can be a continuous sheet of ITO contains an array of regularly spaced holes. The holes are filled in with an electrically insulating material, such as cured photoresist. The electrically insulating layer overcoats the ITO grating so that the upper surface of the structure is completely covered with electrical insulator, and so that the upper surface is substantially flat. When the biosensor 220 is illuminated with light 230, a resonant grating effect is produced on the reflected radiation spectrum 225. The depth and the period of the grating 224 are less than the wavelength of the resonant grating effect.

Figure 10:
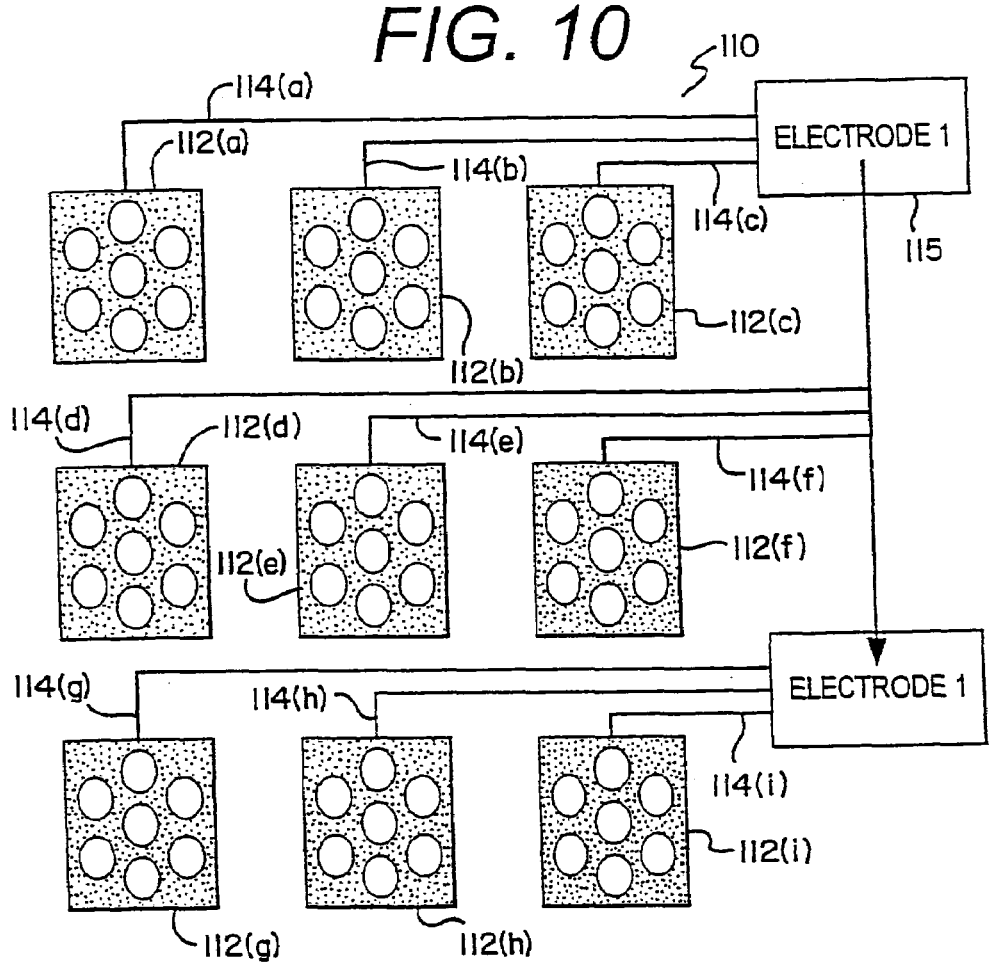
FIG. 10 illustrates an embodiment of an array of biosensor electrodes.

A single electrode can comprise a region containing a plurality of grating periods. For example, FIG. 10 illustrates an embodiment of an array of biosensor electrodes 110. In this preferred embodiment, the array of biosensor electrodes 110 includes 9 grating periods 112(a-i). Providing a plurality of separate grating regions 112(a-i) on a single substrate surface creates an array of biosensor electrodes. Electrical contact to regions 112(a-i) is provided using electrically conducting traces 114(a-i). Traces 114(a-i) are preferably constructed from the same material as a conductor within the biosensor electrode 110. Conducting traces 114(a-i) are coupled to a voltage source 115. Voltage source 115 applies an electrical potential to the various grating regions.

Figure 11:
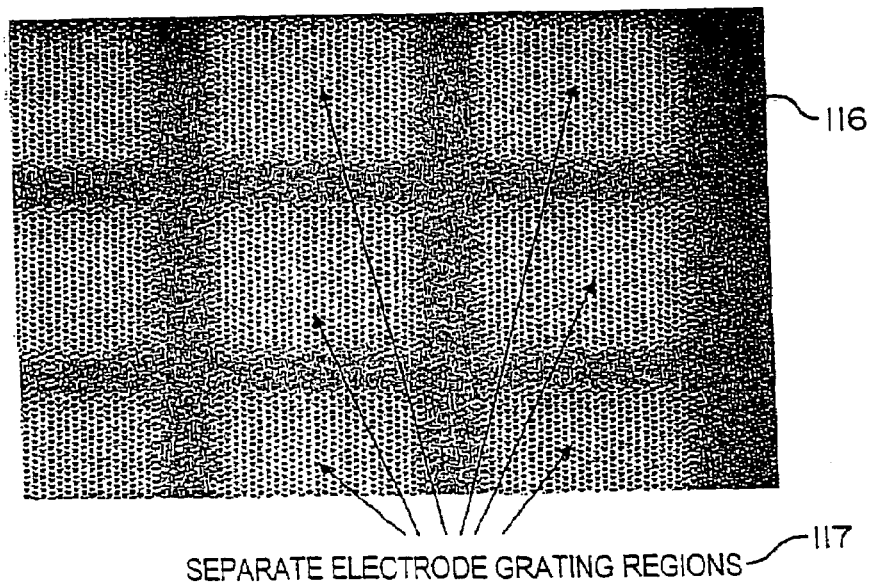
FIG. 11 illustrates a SEM photograph showing a plurality of separate grating regions of an array of biosensor electrodes.

FIG. 11 illustrates a SEM photograph 116 illustrating a plurality of separate grating regions 117(a-f) of an array of biosensor electrodes, such as the electrode illustrated in FIG. 10.

To apply an electrical potential to a biosensor that is capable of attracting or repelling a molecule near the electrode surface, a biosensor upper surface can be immersed in a liquid sample.

Figure 12A:
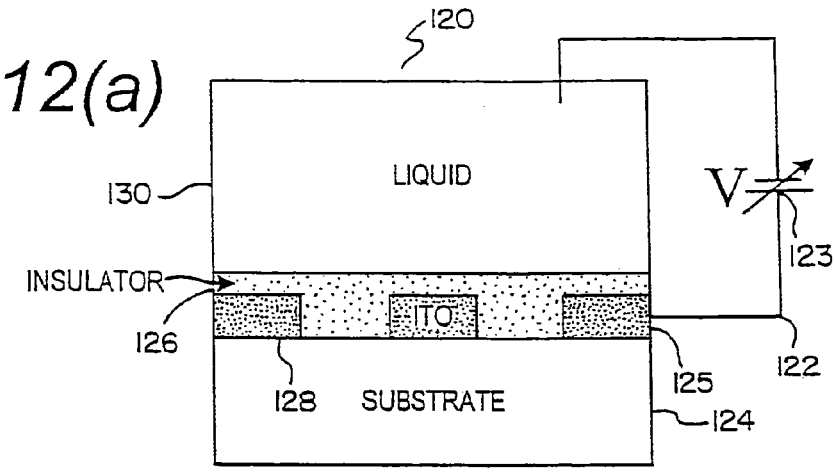
FIG. 12(a) illustrates an embodiment of a biosensor upper surface immersed in a liquid sample.
Figure 12B:
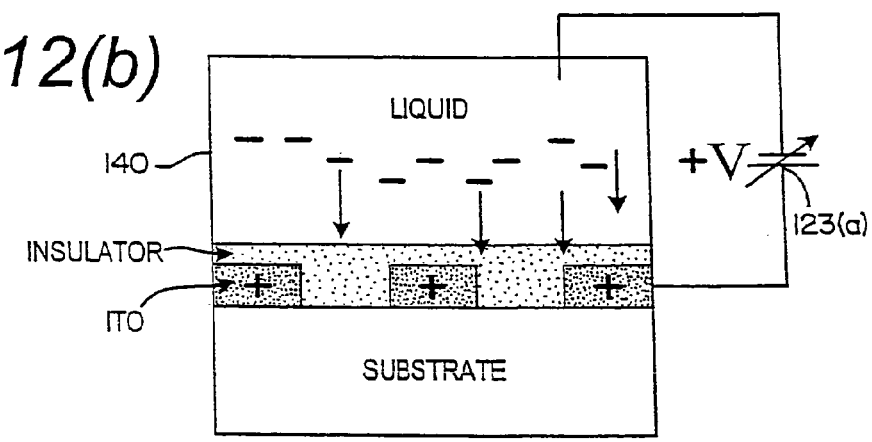
FIG. 12(b) illustrates an attraction of electronegative molecules to a biosensor surface when a positive voltage is applied to the biosensor illustrated in FIG. 12(a).
Figure 12C:
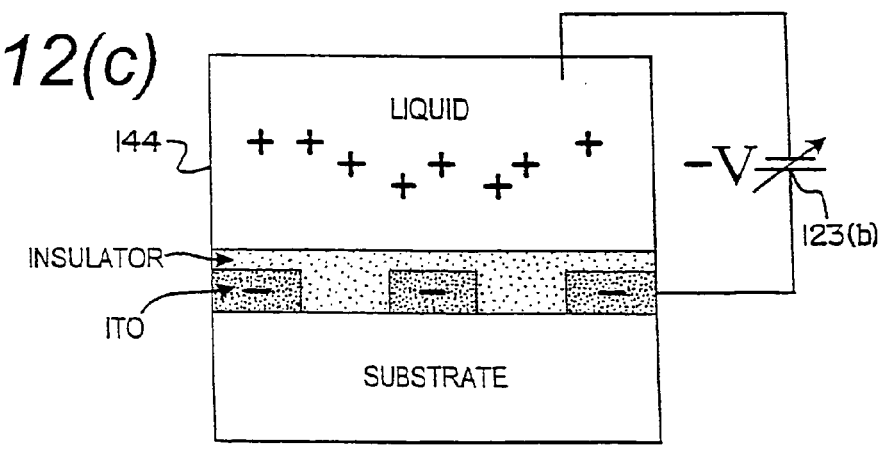
FIG. 12(c) illustrates an application of a repelling force such as a reversed electrical charge to electronegative molecules when a negative electrode voltage is applied to the biosensor illustrated in FIG. 12(a).

FIG. 12(a) illustrates an embodiment of a biosensor upper surface immersed in a liquid sample 130. The biosensor includes a substrate 124, an ITO rating 125, and an insulator 126. A "common" electrode 122 can be placed within the sample liquid 130. A voltage from source 123 can be applied between one selected biosensor electrode region 125 and the common electrode. In this manner, one, several, or all electrodes may be activated or inactivated simultaneously. FIG. 12(b) illustrates the attraction of electronegative molecules 144 to the biosensor surface when a positive voltage is applied to the electrode. FIG. 12(c) illustrates the application of a repelling force such as a reversed electrical charge to electronegative molecules 144 using a negative electrode voltage 123(b).

10. Detection Apparatus and System

Figure 13:
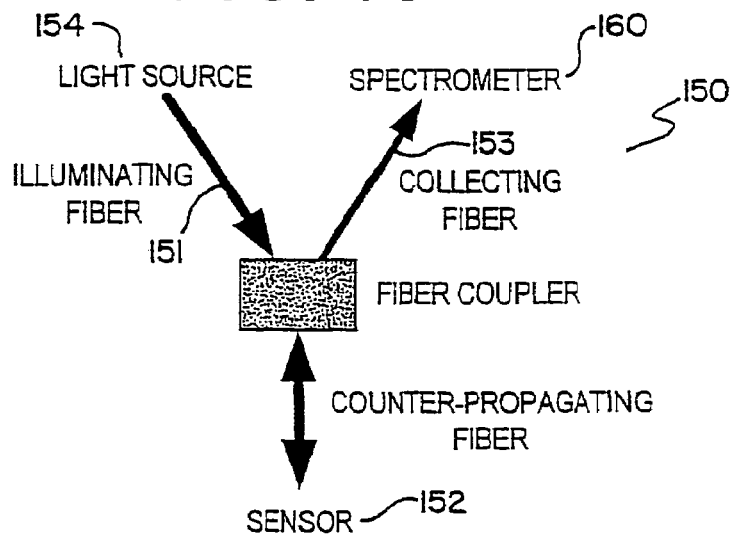
FIG. 13 illustrates an embodiment of a detecting system.

FIG. 13 illustrates one embodiment of a detection system 150. The detection system 150 comprises a biosensor 152 having the structure as previously herein described, e.g., as in FIG. 4. The detection system 150 further includes a light source 154 and spectrometer 160. The light source 154 directs light to the biosensor 152. A detector, such as the spectrometer 160, detects light reflected via a collecting fiber 153 from the biosensor.

The light source 154 illuminates the biosensor 151 via an illuminating fiber 152 from a sensor top surface, i.e., the surface to which one or more specific binding substances are immobilized. Alternatively, the biosensor 152 may be illuminated from its bottom surface. By measuring the shift in resonant wavelength at each distinct location of the biosensor 152, it is possible to determine which distinct locations have binding partners bound to them. The extent of the shift can be used to determine the amount of binding partners in a test sample and the chemical affinity between one or more specific binding substances and the binding partners of the test sample.

In one embodiment, the biosensor 152 is illuminated twice. A first reflected measurement determines the reflectance spectra of one or more distinct locations of a biosensor array with one or more specific binding substances immobilized on the biosensor. A second measurement determines the reflectance spectra after one or more binding partners are applied to a biosensor. The difference in peak wavelength between these two measurements is a measurement of the amount of binding partners that have specifically bound to a biosensor or one or more distinct locations of a biosensor. This method of illumination can account for small nonuniformities in a surface of a biosensor, resulting in regions with slight variations in the peak resonant wavelength. This method can detect varying concentrations or molecular weights of specific binding substances immobilized on a biosensor.

Computer simulation can be used to determine the expected dependence between a peak resonance wavelength and an angle of incident illumination. For example, referring to FIG. 1, substrate 12 may be chosen as glass ($n_{substrate}$=1.50). The grating 16 could be a two-dimensional pattern of silicon nitride squares ($t_2$=180 nm, $n_2$=2.01 (n=refractive index), $k_2$=0.001 (k=absorption coefficient)) with a period of 510 nm, and a filling factor of 56.2% (i.e., 56.2% of the surface is covered with silicon nitride squares while the rest is the area between the squares). The areas between silicon nitride squares may be filled with a lower refractive index material. The same material covers the squares and provides a uniformly flat upper surface. In this embodiment, a glass layer may be selected ($n_1$=1.40) such that it covers the silicon nitride squares by $t_2$=100 nm.

The reflected intensity as a function of wavelength was modeled using GSOLVER software. Such software utilizes full 3-dimensional vector code using hybrid Rigorous Coupled Wave Analysis and Modal analysis. GSOLVER calculates diffracted fields and diffraction efficiencies from plane wave illumination of arbitrarily complex grating structures. The illumination can be from any incidence and any polarization.

Figure 14:
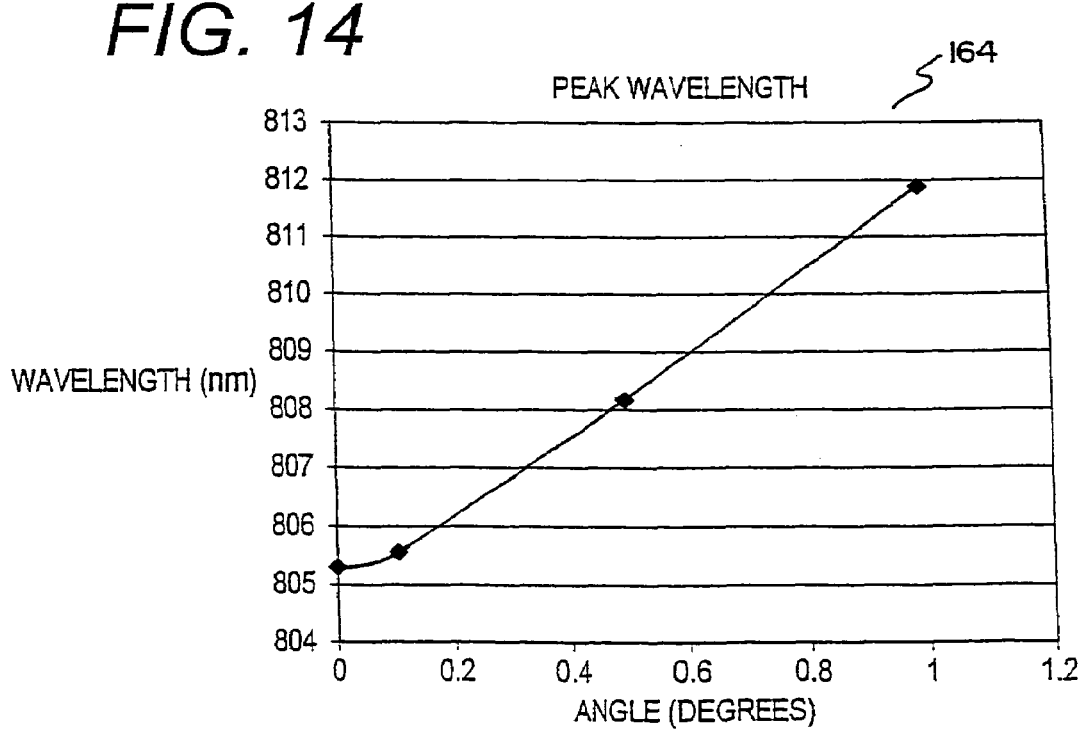
FIG. 14 illustrates resonance wavelength of a biosensor as a function of incident angle of detection beam.

FIG. 14 illustrates a graphical representation 164 of a resonance wavelength of a biosensor measured as a function of incident angle of an illumination beam. The simulation demonstrates that there is a correlation between the angle of incident light, and the measured peak wavelength. This result implies that the collimation of the illuminating beam, and the alignment between the illuminating beam and the reflected beam affects the measured resonant peak linewidth. If the collimation of the illuminating beam is poor, a range of illuminating angles will be incident on the biosensor surface, and a wider resonant peak will be measured than if purely collimated light were incident.

Because the lower sensitivity limit of a biosensor is related to the ability to determine a peak maxima, it is important to measure a narrow resonant peak. Therefore, the use of a collimating illumination system provides increased sensitivity.

It may be desirable for the illuminating and collecting fiber probes to spatially share the same optical path. Several methods may be used to co-locate illuminating and collecting optical paths. For example, one method includes a single illuminating fiber, which may be coupled at its first end to a light source that directs light at the biosensor, and a single collecting fiber, which may be coupled at its first end to a detector that detects light reflected from the biosensor. Each can be coupled at their second ends to a third fiber probe such that this third fiber acts as both an illuminator and a collector. The third fiber probe is oriented at a normal angle of incidence to the biosensor and supports counter-propagating illuminating and reflecting optical signals.

Figure 15:
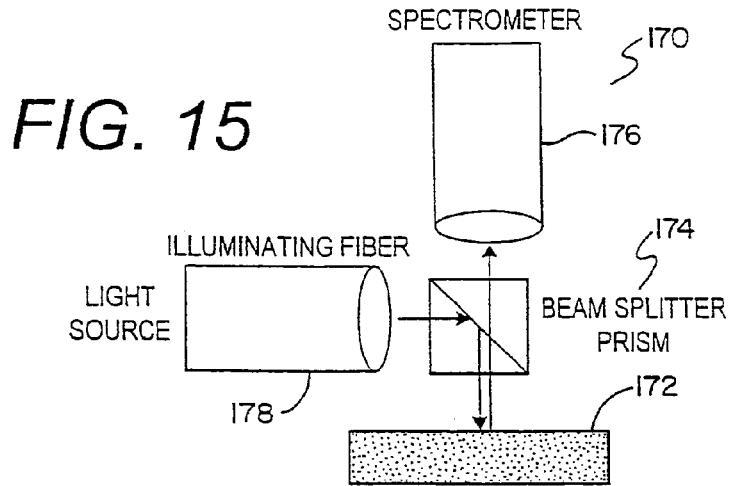
FIG. 15 illustrates an alternative embodiment of a detection system that includes a beam splitter.

FIG. 15 illustrates an alternative embodiment of a detection system 170. In this alternative embodiment, the detection system 170 includes a beam splitter 174. The beam splitter 174 enables a single illuminating fiber 178, which is optically coupled to a light source, to be oriented at a 90 degree angle to a collecting fiber 176. The collecting fiber 176 is optically coupled to a detector. Light is directed through the illuminating fiber probe into the beam splitter, which directs light toward the biosensor 172. The reflected light is directed back into the beam splitter 174, which then directs reflected light into the collecting fiber probe 176.

A beam splitter allows the illuminating light and the reflected light to share a common optical path between the beam splitter and the biosensor.

Figure 17:
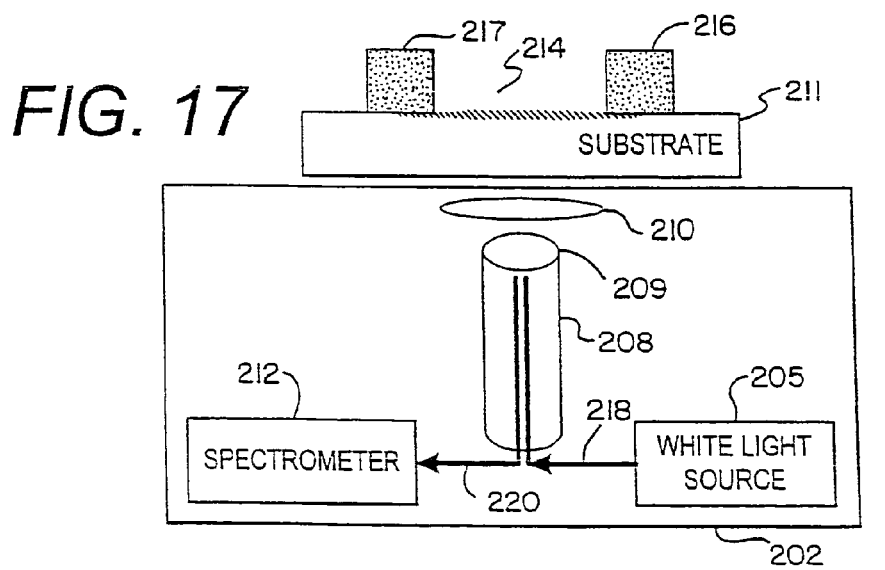
FIG. 17 illustrates an optical fiber probe measuring apparatus.

FIG. 17 illustrates an optical fiber probe measuring apparatus 202. FIG. 17 is a basic design for a PWV detector that can be adapted to a variety of possible instrumentation configurations. Generally, the measuring apparatus 202 includes an instrument that detects biochemical interactions occurring on a surface 215 of an optical biosensor 211. As previously detailed above, the biosensor 211 may be embedded within a bottom portion of a conventional microtiter plate. In one embodiment, the measuring apparatus 202 illuminates the biosensor surface 215 by casting a spot of collimated white light onto the sensor structure 211.

The measuring apparatus 202 collects light reflected from the illuminated biosensor surface. Preferably, the apparatus illuminates and gathers light from multiple locations on the biosensor surface simultaneously. In another embodiment, the apparatus 202 scans the detection head 209 of a dual illumination probe across the biosensor surface. Based on the reflected light, the apparatus measures certain values, such as the peak wavelength values (PWV's), of a plurality of locations within the biosensor embedded microtiter plate.

The biosensor can be incubated in a incubation enclosure and moved to a position for reading. One possible configuration of an instrument that performs incubation and reading is set forth below. Incubation may occur at a user determined temperature. An instrument incorporating the measuring apparatus may also provide a mechanism for mixing samples within a microtiter plate well while the optical sensor resides inside the apparatus. The mixing could take the form of a shaking mechanism or other type of system.

As illustrated in FIG. 17, measuring apparatus 202 includes a white light source 205, an optical fiber probe 208, a collimating lens 210, and a spectrometer 212. A liquid test sample is placed in the space between the structures 216 and 217 for binding to receptors on the surface 215. The measuring apparatus 202 measures biochemical interactions occurring on a surface 215 of the optical device 211. Optical device 211 may have the characteristics of the biosensor devices as herein previously described, such as a well of microtiter plate modified in accordance with FIGS. 8A and 8B. Advantageously, these measurements occur without the use of fluorescent tags or calorimetric labels.

As described in more detail above, the surface 215 of the optical device 211 contains an optical structure such as shown in FIG. 17. When illuminated with collimated white light generated by light source 205, optical device surface 215 is designed to reflect only a narrow band of wavelengths. This narrow band of wavelengths is described as a wavelength peak. The "peak wavelength value" (i.e., PWV) changes when biological material is deposited or removed from the sensor surface 215. That is, the PWV changes when a biological material is deposited between the structures 216 and 217.

The measuring apparatus 202 illuminates distinct locations on the optical device surface with collimated white light, and then collects the reflected light. The collected light is gathered into a wavelength spectrometer 212 for processing, including generation of a PWV.

The measuring apparatus 202 utilizes at least one optical fiber probe 208. Referring now to both FIGS. 17 and 18(a), optical fiber probe 208 can comprise both an illuminating fiber 218 and a detecting fiber 220. The illuminating fiber 218 is optically coupled to the white light source 205 and terminates at a probe head 209 of the optical fiber probe 208. Detecting fiber 220 is optically coupled to a spectrometer 212 and terminates at the probe head 209 of the optical fiber probe 208. In this embodiment, the spectrometer 212 is a single-point spectrometer.

The light source generates white light. The illuminating fiber 218 directs an area of collimated light, via the collimating lens 210, on a sensor surface, preferably a bottom sensor surface. Preferably, the illuminating fiber is bundled along with the second detecting fiber and contained in a unitary optical fiber probe, such as fiber optic probe 208. This detecting fiber 220 is utilized to collect light reflected from the biosensor 211. The detecting fiber 220 channels the reflected light to the spectrometer unit 212, preferably a wavelength spectrometer. The spectrometer unit 212 processes the reflected light to determine a resonance peak wavelength value (i.e., PWV) of the reflected light.

In one preferred embodiment of a measuring apparatus, white light source 205 illuminates a ~1 millimeter (mm) diameter region of the grating region 215 through a 400 micrometer diameter fiber optic and the collimating lens 210 at nominally normal incidence through the bottom of a microtiter plate. Such a microtiter plate could have a standard 96-, 384-, or 1526-well microtiter plate format, but with a biosensor attached to the bottom.

The measuring apparatus 202 illustrated in FIG. 17 includes a single-point optical spectrometer included in the spectrometer unit 212. Preferably, the spectrometer unit 212 includes a commercially available optical spectrometer such as those spectrometers commercially available from Ocean Optics, Inc. Spectrometer 212 includes a diffraction grating and a linear or one dimensional charge coupled device (CCD). The diffraction grating breaks the incident radiation into its component spectra. The boundaries of the spectra may generally range from 680 nanometers (nm) to 930 nm for the device.

The incident radiation impinges a linear (or one dimensional) CCD. In one embodiment, this one dimensional CCD has 2048 pixels. The CCD converts incident radiation into an electric charge. There is a general relationship between the incident radiation and the resulting electric charge: the greater the number of incident photons, the greater the amount of charge the pixels in the CCD accumulate.

Each pixel in the CCD images a separate wavelength of light due to the spatial separation provided by the grating in the spectrometer and the distance between the grating and the CCD. The gap in wavelength imaged by each pixel may range from about 0.13 to about 0.15 nm. Therefore, the first pixel in the CCD images light at a wavelength of 680 nm, the second pixel at 680.13 nm, the third pixel at 680.27 nm, etc. The 2048th pixel, therefore, images light at approximately 930 nm.

The CCD readout consists of an analog voltage signal for each pixel. These analog voltage signals are converted to a digital signal, ranging in value from 0 to 4,095. A digital value of 0 implies that there is no signal (i.e., there is no incident radiation). Conversely, a digital value of 4,095 implies that the pixel is saturated with incident radiation.

A general arrangement of the spectrometer 212 of FIG. 7 is provided in FIG. 18(b). For ease of explanation, the imaging optics inside the spectrometer are not shown in FIG. 18(b). As illustrated in FIG. 18(b), light 221 is incident on the spectrographic grating 222. This light is then reflected in a dispersed fashion 223, 225 along a surface 224 of the CCD 226 with the separation of light in accordance with the shorter wavelength $\lambda_1$ imaged at a first end of the CCD and the longer wavelength $\lambda_2$ imaged at a second end of the CCD.

FIG. 18(c) illustrates a readout of the CCD (Y axis) as a function of pixel number. The curve 229 indicates that there is a peak 231 in pixel output for a particular wavelength $\lambda$ peak. $\lambda$ peak is the peak wavelength value (PWV) referred to herein elsewhere.

Through calibration, one can determine the relationship between wavelength $\lambda$ and the CCD pixel number, the pixel number being represented in FIG. 18(c) along the x-axis. Commercially available wavelength spectrometers, such as the spectrometers commercially available from Ocean Optics, Inc., are provided with information detailing a spectrometer's calibration.

For a given microtiter plate well illuminated by the measuring apparatus 202, the spectrometer provides a curve of CCD readout as a function of $\lambda$ or pixel number. Thus, an instrument will generate data similar to that shown in FIG. 18c and determine PWV for each well or detection location on the sensor.

Figure 19:
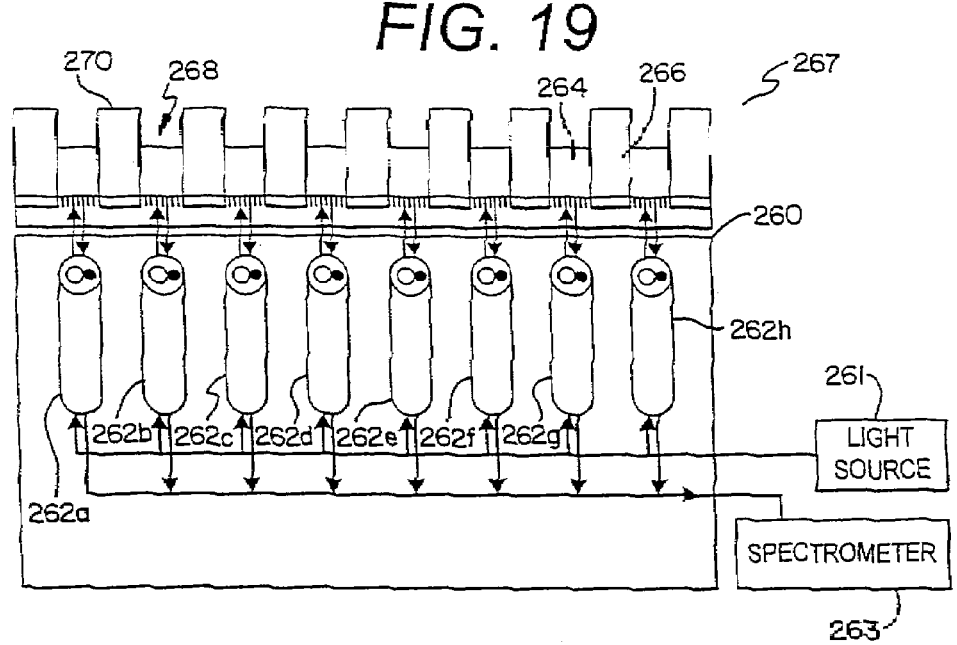
FIG. 19 illustrates an alternative embodiment of a measuring apparatus.

In an alternative embodiment, a measuring apparatus is provided that simultaneously illuminates and measures a plurality of optical device surface regions. In such an alternative embodiment, a plurality of dual probe fibers are utilized. For example, FIG. 19 illustrates an alternative embodiment of a measuring apparatus 260.

Measuring apparatus 260 includes a plurality of dual fiber probes 262(a-h) for illuminating and detecting light reflected from optical device surface. In this embodiment, the apparatus 260 includes eight (8) dual fiber probes designated generally as 262(a-h). However, as those of ordinary skill will realize, measuring apparatus 260 could include alternative dual fiber probe arrangements.

Preferably, dual probe fibers 262(a-h) function as both illuminators and detectors for a single row of microtiter wells provided in bottomless microtiter plate 267. As illustrated, liquid 268 may be provided in a first microtiter plate well 270. For a conventional 96-well microtiter plate, there would be 8 microtiter wells 268(a-h) in this row.

In one embodiment, the measuring apparatus 260 includes a single spectrometer included in spectrometer unit 263 and a single light source 261. Alternatively, measuring apparatus 260 could include a separate spectrometer and a separate CCD for each dual probe fiber: i.e., there are 8 spectrometers and 8 CCDs included in the spectrometer unit 263. Alternatively, the measuring apparatus 260 could include a separate light source for each dual probe in light source unit 261. The processing, measurement, and readout of reflected light for each well is similar to the processing and readout provided in FIG. 18(c).

The measurement system 260 illustrated in FIG. 19 includes a plurality of dual fiber probes 262. Each dual fiber probe operates in a similar fashion as the dual probe illustrated in FIG. 17 and as described above.

Preferably, an algorithm processing the curve illustrated in FIG. 18(c) determines a peak wavelength value with sub-pixel resolution. Sub-pixel resolution is generally preferred since this type of resolution provides peak wavelength values with a precision greater than the CCD pixel separation (i.e., 0.13 to 0.15 nm). A presently preferred algorithm is set forth in section 12 below.

In the dual fiber probe embodiment illustrated in FIG. 19, each dual probe 262 (a-h) includes an illuminating fiber and a detecting fiber. In this preferred embodiment, the apparatus 260 is configured to include eight dual fiber probes and therefore provides a separate readout per dual probe. In such a configuration, eight dual fiber probes simultaneously illuminate a single row of a standard microtiter plate and measure light reflected from this illuminated row. As those of ordinary skill will realize, other multiple probe configurations may also be utilized.

The plurality of dual probes may be arranged side by side in a linear fashion. By utilizing such a linear arrangement, a plurality of dual probes can simultaneously illuminate and then read out a plurality of sensor surface locations. For example, a linear probe arrangement may be utilized to illuminate and then read an entire row or an entire column of a microtiter plate. In this preferred embodiment, each dual probe head contains two optical fibers. The first fiber is connected to a white light source to cast a small spot of collimated light on the sensor surface. The second fiber reflects the reflected radiation and supplies it to a spectrometer. After one row is illuminated, relative motion occurs between the detector probes and the sensor (microtiter plate) and the next row or column of the sensor is read. The process continues until all rows (or columns) have been read.

As will be described in further detail below, in one embodiment of the measuring apparatus, a microtiter plate is placed on a linear motion stage. The linear motion stage moves the microplate in a specified, linear scan direction. As the microtiter plate is moved in this scan direction, each microplate column is sequentially illuminated. The resulting reflected light is measured. In one preferred embodiment, a scan of a conventional 96-well microtiter plate may take approximately 15 to 30 seconds to illuminate and measure the resultant reflected spectrum.

Figure 20:
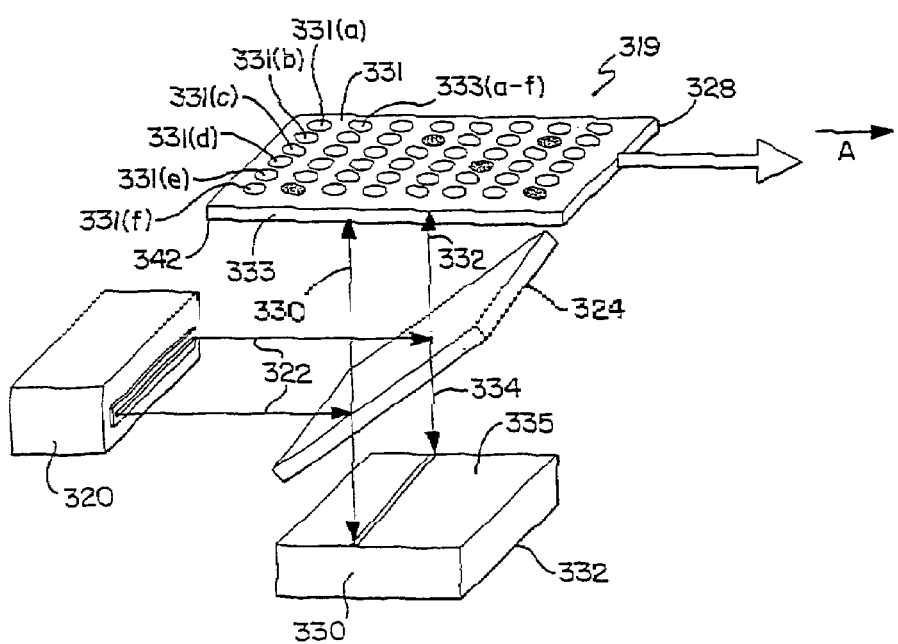
FIG. 20 illustrates yet another alternative embodiment of a measuring apparatus.

In yet another alternative embodiment, an imaging apparatus utilizes a spectrometer unit that comprises an imaging spectrometer. For example, FIG. 20 illustrates an alternative embodiment of a biosensor instrument system 319. The instrument system 319 includes an imaging spectrometer 332. One advantage of the imaging spectrometer system is that such imaging systems reduce the amount of time for generating a PWV image. Another advantage is to study biological binding of an area in a non-uniform fashion.

The instrument system 319 illustrated in FIG. 20 includes a collimated white light source 320, a beam splitter 324, and an imaging spectrometer 330. Beam splitter 324 redirects the collimated light 322 towards a biosensor in accordance with principles discussed previously. In one embodiment, the biosensor 319 is a conventional microarray chip 328. More preferably, the microarray chip could comprise a plurality of wells or spots arranged in an array of uniform rows and columns.

Imaging spectrometer 332 is used to generate a PWV image for each of the receptor locations (spots) contained in a microarray chip 328. In this embodiment, the microarray chip 328 comprises a plurality of spotw arranged in eight (8) rows, where each row contains six (6) spotw. For example, a first microarray chip row 331 contains six spotw 331(a-f). Similarly, a second microarray chip row 333 contains six spotw 333(a-f). All the spotw of each row can be simultaneously illuminated incident light 332. As those of ordinary skill in the art will recognize, the total number of spots on a microarray chip can be much larger, routinely in the tens of thousands.

Light 322 is collimated and directed towards the beam splitter 324. The beam splitter 324 allows the collimated light 322 and the reflected light 334 to share a common optical path between the beam splitter and the microarray chip 328.

Preferably, the collimated light is directed at the sensor bottom surface 342 at normal incidence via the beam splitter 324. Normally reflected light 334 is collected into an input 335 of the imaging spectrometer 332.

At the microarray chip 328, redirected light 330 illuminates an imaging area 332 along a bottom surface 342 of the microarray chip 328. The redirected light 330 is used to illuminate this imaging area 332. In this embodiment, the illuminated imaging area 332 may be defined by a plurality of spotw 331 along the microarray chip 328. Preferably, the illuminated imaging area 332 is defined by either a complete row or a complete column of spotw contained on the microarray chip 328. For example, illuminated imaging area 332 could be defined to include the first microarray chip row 331 or row 333.

The bottom surface 342 of the microarray chip 328 is scanned in a sequential manner. To accomplish a complete scan of the bottom surface 342, the microarray chip 328 is transported along a scan direction "A." As the microarray chip 328 is transported along this scan direction, the collimated light 330 traverses along the complete length of the bottom surface 342 of the microarray chip. In this manner, the instrument system 319 sequentially illuminates and reads out all of the spotw in a microarray chip 328. For example, as the chip 328 is moved in the "A" scan direction, chip row 333 is first illuminated and read out, and then chip row 331 is illuminated and then read out. The process continues until all rows are read.

Preferably, the illuminated imaging area includes all the spotw along a microarray row. For example, at a given point in time, the redirected light may illuminate a first row of spotw on the 8×6 microarray chip. Consequently, light 330 illuminates all six spotw 331(a-f) contained in the first row 331 of the microarray chip 328. As the microarray chip 328 is transported along scan direction A, the collimated white light source 320 simultaneously illuminates all of the spotw contained in the next microarray row. To complete the read out of the entire microarray chip, each of the eight (8) rows of the microarray chip are sequentially illuminated.

The spectrometer unit 332 preferably comprises an imaging spectrometer containing a two-dimensional Charge Coupled Device (CCD) camera and a diffraction grating. The reflected light 334 containing the biosensor resonance signal for each spot is diffracted by the grating in the spectrometer unit. The diffraction produces a spatially segregated wavelength spectra for each point within the illuminated area. (See, e.g., FIG. 18(c). The wavelength spectrum has a second spatial component corresponding to the direction transverse to the scan direction "A." This second spatial component is subdivided into discrete portions corresponding to spotw in this transverse direction.

For example, if the imaging spectrometer includes a CCD camera that contains 512×2048 imaging elements, then an illuminating line is spatially segregated into 512 imaging elements or points. A wavelength spectra is measured for each of the 512 imaging elements or points along the orthogonal axis of the CCD camera Where the CCD camera contains 512×2048 imaging elements, the CCD would have a resolution of 2048 wavelength data points. Using this method, the PWV's of 512 points are determined for a single "line" or imaging area across the sensor bottom surface 342. For a conventional CCD imaging camera typically having spatial resolution of approximately 10 microns, a 1:1 imaging system is capable of resolving PWV values on sensor surface 342 with a 10 micron resolution. In order to measure a PWV image of the entire sensor bottom surface 342, the sensor 328 is transported along an imaging plane (scan direction A), and subsequent line scans are used to construct a PWV image.

Figure 21:
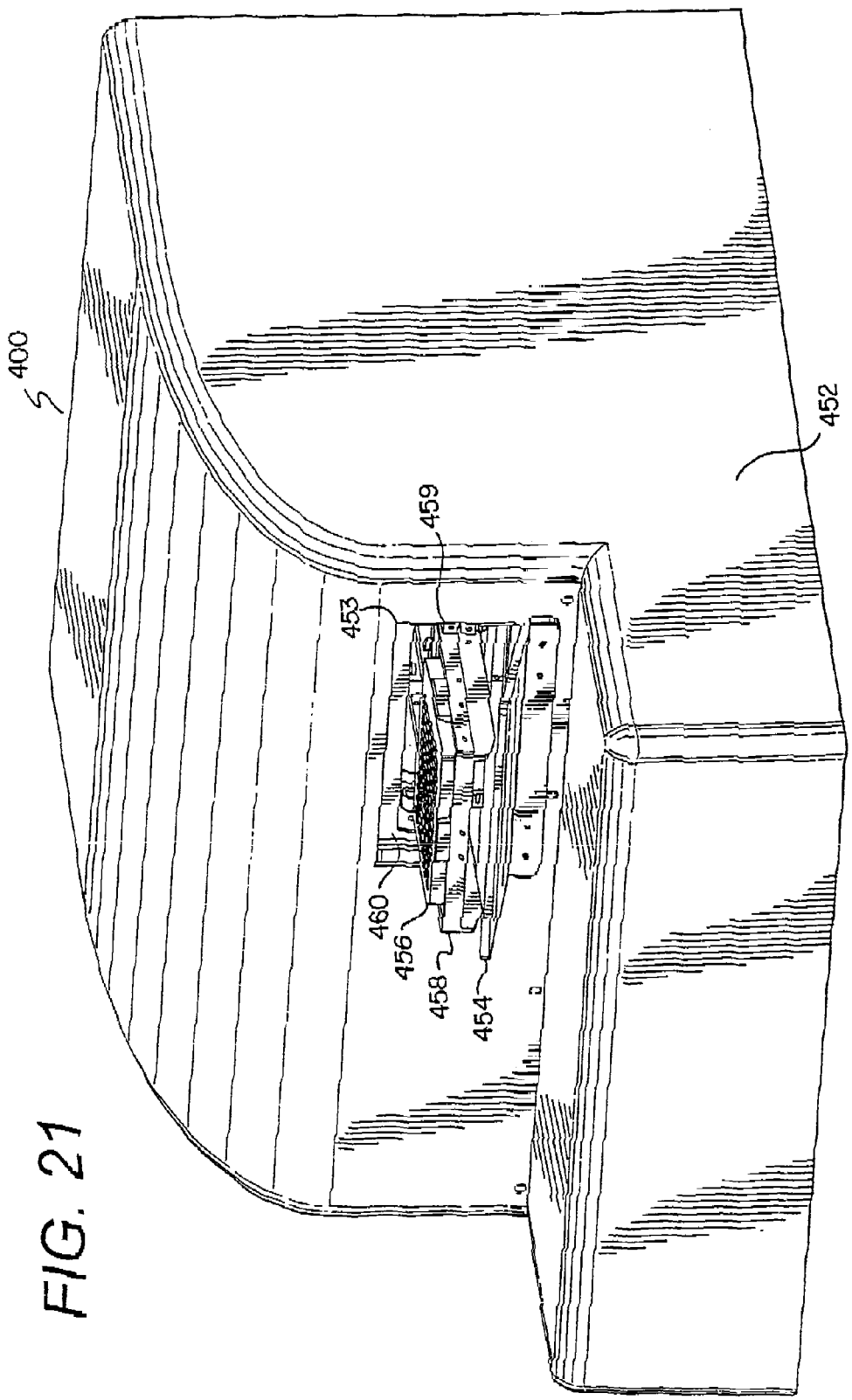
FIG. 21 illustrates an alternative embodiment of an instrument for detection of biomolecular interactions in accordance with one possible embodiment.

FIGS. 21-24 illustrate various aspects of yet another alternative embodiment of a measuring instrument 400 which incorporates various principles of FIG. 19. FIG. 21 illustrates a perspective view of the measuring instrument 400.

Measuring instrument 400 includes a measuring instrument cover 452 and a door 454. A microplate well plate (or microtiter plate) 456 configured as a biosensor in accordance with this invention is shown in an extracted position, outside an incubator assembly 460 incorporated in the measuring instrument 400. The microplate well plate 456 is held by a microwell tray 458. The tray 458 may extend out of the incubator assembly 460 through a door way 453 located at the front of the incubator assembly 460. The incubator assembly 460 allows the tray 458 to be maintained at a user defined temperature during microwell tray read out and/or measurement.

In one preferred embodiment, incubator assembly 460 is used for performing assays at controlled temperatures, typically such controlled temperatures may range from 4 and 45 degrees Celsius. As will be explained with reference to FIGS. 22, 23, and 24, a collimator assembly 708 is positioned preferably beneath a bottom portion 602 of the incubator assembly 460. During microtiter well illumination and wavelength measurement, the collimator assembly 708 illuminates a bottom surface 459 of the tray 458.

Figure 22:
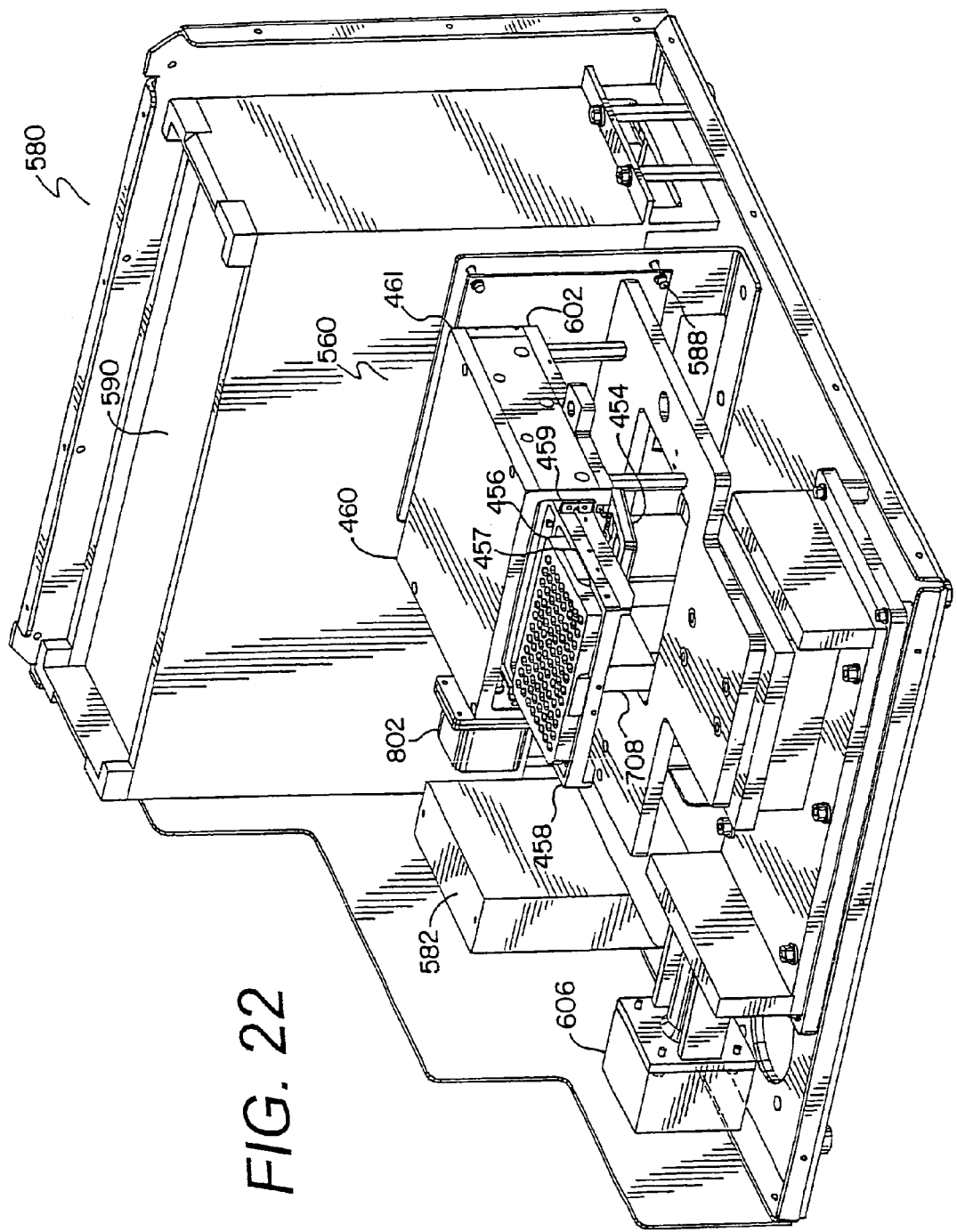
FIG. 22 illustrates a perspective view of the measuring apparatus illustrated in FIG. 21.

While the tray 458 remains in an extracted position outside of the incubator assembly 460, the microtiter plate 456 may be placed on or removed from the tray 458. The plate 456 may be held in the tray 458 via a set of registration points, spring clips, or other known types of securing means. In FIG. 22, clips 457 are used to hold the plate 456 in the tray 458.

After the microtiter plate 456 has been loaded with a fluid sample with biological material to be detected and measured, the tray 458 is transported into the incubator assembly 460. Processing, mixing, heating, and/or readout of the biosensors may then begin, preferably under the control of the controller assembly 588 (see FIG. 22).

Once the tray 458 retracts into the incubator assembly 460, the tray remains stationary during illumination and read out. For a readout of the microtiter plate 456 to occur, the collimator assembly 708 generates an illumination pattern that is incident along the bottom surface 459 of the plate 456. Preferably, the measuring apparatus 400 generates a beam of light that is incident along an entire row of wells of the plate 456.

Alternatively, the measuring apparatus 400 generates a plurality of illumination beams that are simultaneously incident on a plurality of plate wells. The illumination pattern, comprising multiple beams, is generated by dual illumination fiber optic probes contained within the collimator assembly 708. The construction of the probes is as shown is FIG. 17. As previously herein described, the light reflected off of the biosensor surface may then be detected by the same plurality of probes contained within a collimator assembly 708. This reflected light is then analyzed via the spectrometer system 590.

Figure 24:
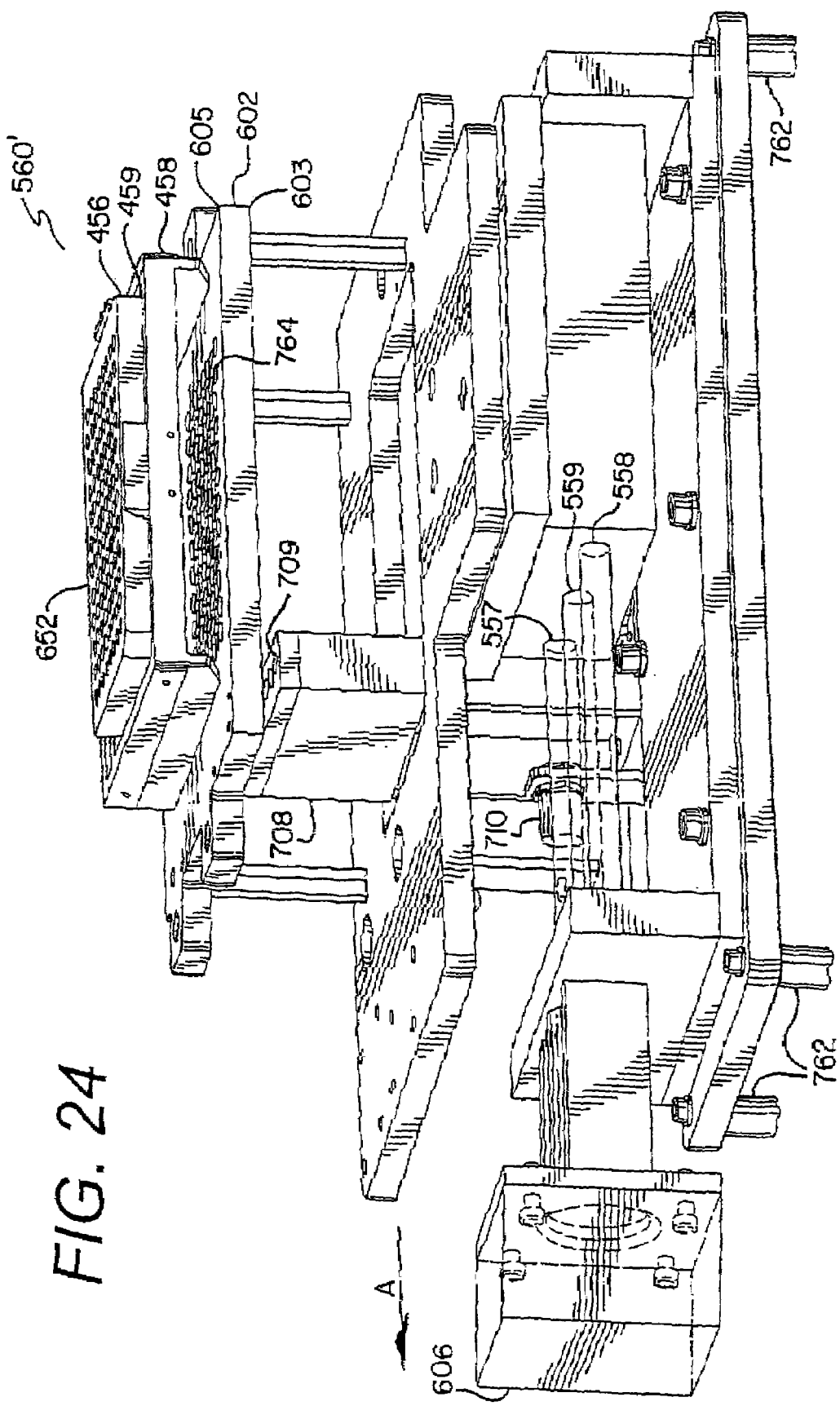
FIG. 24 illustrates a perspective view of the transition stage assembly of FIG. 23 with an incubator assembly top portion removed.

The incubator assembly 460 is provided with a plurality of apertures 764 along a bottom incubator assembly structure. As can be seen in FIG. 24, incubator assembly apertures 764 are configured to generally line-up and match the well locations 657 on the plate 456 when the plate 456 is in a readout position within the incubator assembly 460. For example, if there are 96 wells on the microwell well plate 456, the incubator assembly bottom portion 602 will be provided with 96 apertures 764. These apertures will be configured in the same type of array as the wells of the well plate (e.g., 8 rows by 6 columns). These apertures 764 provide clearance for light generated by collimator assembly 708 to reach the wells from the illuminating probes 709.

To enable user access to the tray and to the plate, the plate tray 458 extends out of the measuring apparatus 400. The tray 458 can be retracted into the apparatus 400 and the door cover 454 closed to begin microplate processing. Such processing could include mixing liquid in the microtiter wells, heating deposited liquids to a predetermined temperature, illumination of the microplate 456, and processing various reflected illumination patterns.

FIG. 22 illustrates a perspective view 580 of various internal components of the measuring instrument 400 illustrated in FIG. 21. As shown in FIG. 22, internal components of the measuring instrument 580 include a transition stage assembly 560, heater controller unit 582, a controller board assembly 588, and a spectrometer unit 590. The transition stage assembly 560 includes the incubator assembly 460 and the collimator assembly 708. The heater controller unit 582, the controller board assembly 588, the transition stage assembly 560, and the spectrometer unit 590 are mounted on a base plate 592. The microplate well tray 556 is shown in the retracted position, outside of the incubator assembly 460.

The heater controller unit 582 provides temperature control to the incubator assembly 460. The controller board assembly 588 provides functional controls for the measuring apparatus including the mixing and other motion controls related to translation stage 560 and tray handling 458.

The spectrometer unit 590 contains an appropriate spectrometer for generating the PWV data. The design of the spectrometer will vary depending on the illumination source. If the probes of FIG. 17 are used, the spectrometer will ordinarily have the design shown in FIG. 18B.

Figure 23:
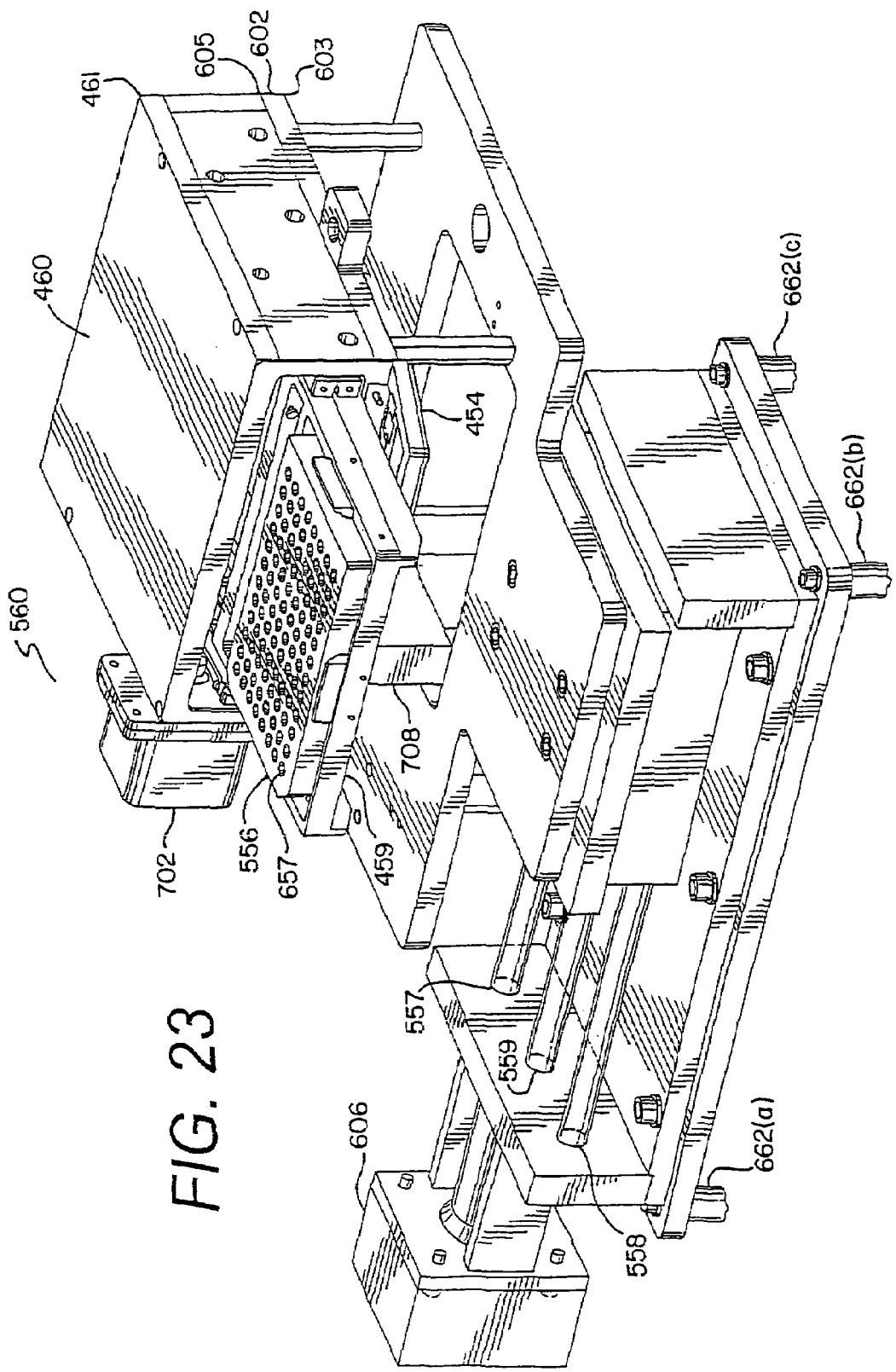
FIG. 23 illustrates a perspective view of the transition stage assembly illustrated in FIG. 22.

FIG. 23 illustrates a perspective view of the transition stage assembly 560 of the measuring instrument 400 illustrated in FIGS. 21 and 22. FIG. 26 illustrates the transition stage assembly 560 of FIG. 23 with an incubator assembly top portion 461 removed (See FIGS. 22 and 23). As can be seen from FIGS. 23 and 24, the transition stage assembly 560 includes the microwell tray 458 positioned in the retracted position. The microwell tray 458 has a plurality of wells 657, enters the incubation assembly 460 (FIG. 23) to initiate the read out process.

The microwell plate tray 458 is mounted on a top surface 605 of a bottom portion 602 of the incubator assembly 460. Preferably, where the microtiter tray 456 is a conventional microtiter tray having 96 wells, the bottom portion 602 of the incubator assembly 460 includes 96 holes. The microwell plate tray 458 is positioned over the bottom portion of the incubator assembly 602 such that the incubator assembly apparatus essentially matches up with the apertures (wells) contained in the microwell tray 458. Alternately, bottom portion 602 may contain a transparent section that matches the bottom portion of the plate, or may eliminate the bottom portion.

During specimen illumination and measurement, the microwell tray 458 is preferably held in a stationary manner within the incubator assembly 460 by the bottom incubator assembly portion 602. During illumination and measurement, the collimator assembly 708 is held in a stationary manner while a stepping motor 606 drives the incubator assembly, including the plate, in a linear direction "A". As the incubator assembly 460 is driven along direction "A," the collimator assembly 708 illuminates the bottom surface 459 of microtiter plate 456. The resulting reflected illumination patterns are detected by the collimator assembly 708. A home position sensor 710 is provided as a portion of the translation stage assembly and to determine the position during the illumination process.

The transition stage assembly 760 is provided with a plurality of elastomer isolators 762. In this embodiment, a total of six elastomer isolators are used to provide isolation and noise reduction during illumination and read out.

As can be seen from FIGS. 23 and 24, the collimator assembly 708 is positioned below a bottom surface 603 of the incubator portion bottom portion 602. Preferably, the collimator assembly 708 includes a plurality of dual fiber probe heads 709. In the embodiment illustrated in FIG. 24, the collimator assembly 708 includes 8 dual fiber probe heads 709. These dual fiber probes could have a probe head configuration similar to the fiber optic probes illustrated in FIG. 19 and as previously described. Alternatively, the collimator assembly 708 could include a PWV imaging system such as the PWV imaging system illustrated in FIG. 20.

For ease of explanation, only the bottom plate 602 of the incubator assembly 460 is shown is FIG. 24. The incubator assembly bottom portion 602 is provided with a plurality of apertures 764. Preferably, where the microwell plate 456 is provided with an 8×12 array of wells such as illustrated in FIG. 24, the incubator assembly bottom portion 602 will also include an 8×12 array of 96 apertures. These apertures will essentially match the 96 wells on the microwell plate 456. In this manner, the collimated white light generated by the collimator assembly 708 propagates through a first surface 603 along the incubator assembly bottom portion 602, and exit a second surface or top surface 605 of incubator assembly bottom portion 602. The collimated light can then illuminate a bottom well portion of the microwell plate 456. Alternately, bottom portion 602 may contain a transparent section that matches the bottom portion of the plate, or may eliminate the bottom portion.

Referring to FIGS. 23 and 24, a drive motor 606 is provided for driving the incubator assembly during well scanning. A home position sensor 710 is provided as a stop measuring during the translation stage. The plate handling stage uses a stepping motor 702 to drive a rack-and-pinion mechanism. The scanning stage uses a stepping motor 606 to drive a leadscrew 559 along translation stage rails 557, 558.

A mixer assembly may be used for mixing the liquid in the wells. In the present invention, a mixing mechanism is located between the incubation chamber of the translation stage. Additionally, a mixing mechanism may be provided in an alternative location.

Figure 25:
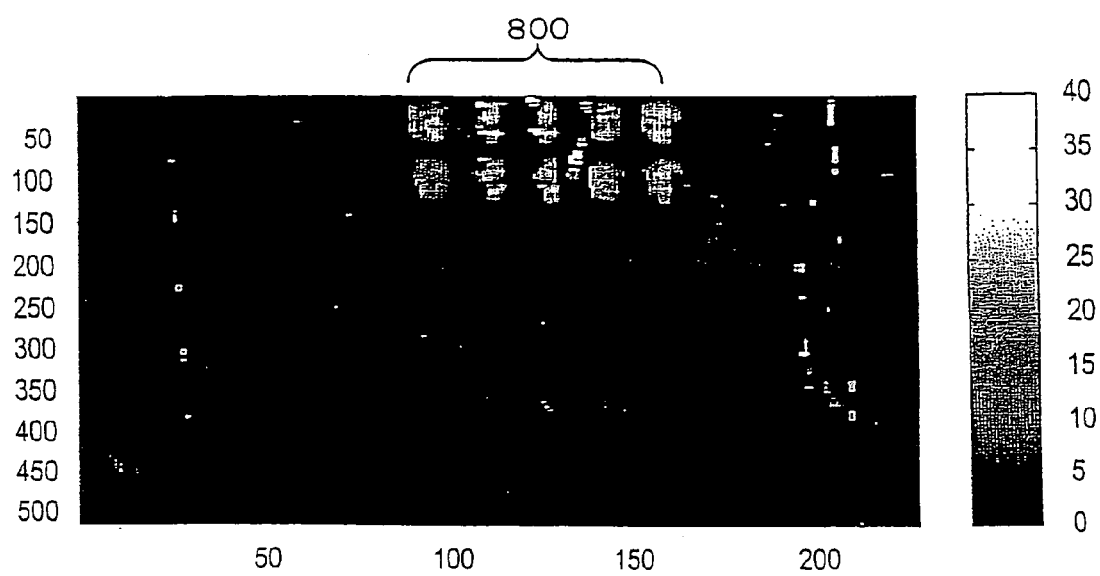
FIG. 25 illustrates a visualization of a spotted micro-array image.

FIG. 25 illustrates an example of a microarray image. Specifically, FIG. 25 illustrates ten spots 800 of human-IgG spotted on a TaO sensor surface. Each spot is approximately 400-microns in diameter. FIG. 25 illustrates the result of subtracting a pre-spotted image from a post-spotted image. The intensity scale conversion factor is illustrated to be a 0.04 nm per display intensity unit, resulting in a detected wavelength shift of 0.8 nm.

11. Angular Scanning

The proposed detection systems are based on collimated white light illumination of a biosensor surface and optical spectroscopy measurement of the resonance peak of the reflected beam. Molecular binding on the surface of a biosensor is indicated by a shift in the peak wavelength value, while an increase in the wavelength corresponds to an increase in molecular absorption.

As shown in theoretical modeling and experimental data, the resonance peak wavelength is strongly dependent on the incident angle of the detection light beam. Because of the angular dependence of the resonance peak wavelength, the incident white light needs to be collimated. Angular dispersion of the light beam broadens the resonance peak, and could reduce biosensor detection sensitivity. In addition, the signal quality from the spectroscopic measurement could depend on the power of the light source and the sensitivity of the detector. In order to obtain a desirable signal-to-noise ratio, a lengthy integration time for each detection location may be required, and therefore lengthen overall time to readout a biosensor plate. A tunable laser source can be used for detection of grating resonance, but is generally cost prohibitive.

In one embodiment, these disadvantages are addressed by using a laser beam for illumination of a biosensor, and a light detector for measurement of reflected beam power. A scanning mirror device can be used for varying the incident angle of the laser beam, and an optical system is used for maintaining collimation of the incident laser beam. See, e.g., "Optical Scanning" (Gerald F. Marchall ed., Marcel Dekker (1991). Any type of laser scanning can be used. For example, a scanning device that can generate scan lines at a rate of about 2 lines to about 1,000 lines per second is useful in the invention. In one embodiment of the invention, a scanning device scans from about 50 lines to about 300 lines per second.

In one embodiment, the reflected light beam passes through part of the laser scanning optical system, and is measured by a single light detector. The laser source can be a diode laser with a wavelength of, for example, 780 nm, 785 nm, 810 nm, or 830 nm. Laser diodes such as these are readily available at power levels up to 150 mW, and their wavelengths correspond to high sensitivity of Si photodiodes. The detector thus can be based on photodiode biosensors.

In another detection system embodiment, while a scanning mirror changes its angular position, the incident angle of the laser beam on the surface changes by nominally twice the mirror angular displacement. The scanning mirror device can be a linear galvanometer, operating at a frequency of about 2 Hz up to about 120 Hz, and mechanical scan angle of about 10 degrees to about 20 degrees. In this example, a single scan can be completed within about 10 msec. A resonant galvanometer or a polygon scanner can also be used.

The angular resolution depends on the galvanometer specification, and reflected light sampling frequency. Assuming galvanometer resolution of 30 arcsec mechanical, corresponding resolution for biosensor angular scan is 60 arcsec, i.e. 0.017 degree. In addition, assume a sampling rate of 100 ksamples/sec, and 20 degrees scan within 10 msec.

As a result, the quantization step is 20 degrees for 1000 samples, i.e. 0.02 degree per sample. In this example, a resonance peak width of 0.2 degree, as shown by Peng and Morris (Experimental demonstration of resonant anomalies in diffraction from two-dimensional gratings, *Optics Lett.*, 21:549 (1996)), will be covered by 10 data points, each of which corresponds to resolution of the detection system.

The advantages of such a detection system includes: increased collimation of incident light by a laser beam, high signal-to-noise ratio due to high beam power of a laser diode, low cost due to a single element light detector instead of a spectrometer, and high resolution of resonance peak due to angular scanning.

12. Mathematical Resonant Peak Determination

The sensitivity of a biosensor is determined by the shift in the location of the resonant peak when material is bound to the biosensor surface. Because of noise inherent in the spectrum, it is preferable to use a procedure for determining an analytical curve—the turning point (i.e., peak) of which is well defined. Furthermore, the peak corresponding to an analytic expression can be preferably determined to greater than sub-sampling-interval accuracy, providing even greater sensitivity.

One embodiment utilizes a method for determining a location of a resonant peak for a binding partner in a resonant reflectance spectrum with a colormetric resonant biosensor. The method comprises selecting a set of resonant reflectance data for a plurality of colormetric resonant biosensors or a plurality of biosensor distinct locations. The set of resonant reflectance data is collected by illuminating a colormetric resonant diffractive grating surface with a light source and measuring reflected light at a pre-determined incidence. The colormetric resonant diffractive grating surface is used as a surface binding platform for one or more specific binding substances such that binding partners can be detected without use of a molecular label.

The step of selecting a set of resonant reflectance data can include selecting a set of resonant reflectance data:

a. $x_i$ and $y_i$ for i=1, 2, 3, . . . n, b. wherein $x_i$ is a first measurement includes a first reflectance spectra of one or more specific binding substances attached to the colormetric resonant diffractive grating surface, $y_i$ is a second measurement and includes a second reflectance spectra of the one or more specific binding substances after a plurality of binding partners are applied to colormetric resonant diffractive grating surface including the one or more specific binding substances, and n is a total number of measurements collected.

The set of resonant reflectance data includes a plurality of sets of two measurements, where a first measurement includes a first reflectance spectra of one or more specific binding substances that are attached to the colormetric resonant diffractive grating surface and a second measurement includes a second reflectance spectra of the one or more specific binding substances after one or more binding partners are applied to the colormetric resonant diffractive grating surface including the one or more specific binding substances. A difference in a peak wavelength between the first and second measurement is a measurement of an amount of binding partners that bound to the one or more specific binding substances. A sensitivity of a colormetric resonant biosensor can be determined by a shift in a location of a resonant peak in the plurality of sets of two measurements in the set of resonant reflectance data A maximum value for a second measurement from the plurality of sets of two measurements is determined from the set of resonant reflectance data for the plurality of binding partners, wherein the maximum value includes inherent noise included in the resonant reflectance data. A maximum value for a second measurement can include determining a maximum value $y_k$ such that:

c. $(y_k \geq y_i)$ for all i, $\neq k$.

The algorithm determines whether the maximum value is greater than a pre-determined threshold. This can be calculated by, for example, computing a mean of the set of resonant reflectance data; computing a standard deviation of the set of resonant reflectance data; and determining whether $((y_k\text{-mean})/\text{standard deviation})$ is greater than a predetermined threshold. The pre-determined threshold is determined by the user. The user will determine what amount of sensitivity is desired and will set the pre-determined threshold accordingly.

If the maximum value is greater than a pre-determined threshold a curve-fit region around the determined maximum value is defined. The step of defining a curve-fit region around the determined maximum value can include, for example:

d. defining a curve-fit region of (2w+1) bins, wherein w is a pre-determined accuracy value;
e. extracting $(x_i,$ k–w<=i<=k+w); and
f. extracting $(y_i,$ k–w<=i<=k+w).

A curve-fitting procedure is performed to fit a curve around the curve-fit region, wherein the curve-fitting procedure removes a pre-determined amount of inherent noise included in the resonant reflectance data. A curve-fitting procedure can include, for example:

g. computing $g_i = \ln y_i$;
h. performing a $2^{nd}$ order polynomial fit on $g'_i$ to obtain $g'_i$ defined on
i. $(x_i,$ k–w<=i<=k+w);
j. determining from the $2^{nd}$ order polynomial fit coefficients a, b and c of for $(ax^2+bx+c)$-; and
k. computing $y'_i = e^{g'_i}$.

The location of a maximum resonant peak is determined on the fitted curve, which can include, for example, determining a location of maximum reasonant peak $(x_p = (-b)/2a)$. A value of the maximum resonant peak is determined, wherein the value of the maximum resonant peak is used to identify an amount of biomolecular binding of the one or more specific binding substances to the one or more binding partners. A value of the maximum resonant peak can include, for example, determining the value with of $x_p$ at $y'_p$.

Alternatively, peak values of the measurement apparatus embodiments may be derived by the mathematical resonant peak determination described in commonly assigned related copending patent application Ser. No.10/253,846 (MBHB 01-1775), the entirety of which is herein incorporated by reference and to which the reader is directed for further information.

One embodiment of the measurement apparatus includes a computer readable medium having stored therein instructions for causing a processor to execute a method for determining a location of a resonant peak for a binding partner in a resonant reflectance spectrum with a colormetric resonant biosensor. A computer readable medium can include, for example, magnetic disks, optical disks, organic memory, and any other volatile (e.g., Random Access Memory ("RAM")) or non-volatile (e.g., Read-Only Memory ("ROM")) mass storage system readable by the processor. The computer readable medium includes cooperating or interconnected computer readable medium, which exist exclusively on a processing system or to be distributed among multiple interconnected processing systems that can be local or remote to the processing system.

The following are provided for exemplification purpose only and are not intended to limit the scope of the invention described in broad terms above. All references cited in this disclosure are incorporated herein by reference.

Sensor Readout Instrumentation

In order to detect reflected resonance, a white light source can illuminate an approximately 1 mm diameter region of a biosensor surface through a 400 micrometer diameter fiber optic and a collimating lens. Smaller or larger areas may be sampled through the use of illumination apertures and different lenses. A group of six detection fibers may be bundled around the illumination fiber for gathering reflected light for analysis with a spectrometer (Ocean Optics, Dunedin, Fla.). For example, a spectrometer can be centered at a wavelength of 800 nm, with a resolution of approximately 0.14 nm between sampling bins. The spectrometer integrates reflected signal for 25-75 msec for each measurement. The biosensor sits upon an x-y motion stage so that different regions of the biosensor surface can be addressed in sequence.

Equivalent measurements can be made by either illuminating the top surface of device, or by illuminating through the bottom surface of the transparent substrate. Illumination through the back is preferred when the biosensor surface is immersed in liquid, and is most compatible with measurement of the biosensor when it is incorporated into the bottom surface of, for example, a microwell plate.

Mathematical Resonant Peak Determination

This example discusses some of the findings that have been obtained from looking at fitting different types of curves to the observed data.

The first analytic curve examined is a second-order polynomial, given by $$y = ax^2 + bx + c$$

The least-squares solution to this equation is given by the cost function $$\phi = \sum_{i=1}^{n}(ax_i^2 + bx_i + c - y_i)^2,$$

the minimization of which is imposed by the constraints $$\frac{\partial \phi}{\partial a} = \frac{\partial \phi}{\partial b} = \frac{\partial \phi}{\partial c} = 0.$$

Solving these constraints for a, b, and c yields $$\begin{pmatrix} a \\ b \\ c \end{pmatrix} = \begin{pmatrix} \sum x_i^4 & \sum x_i^3 & \sum x_i^2 \\ \sum x_i^3 & \sum x_i^2 & \sum x_i \\ \sum x^2 & \sum x_i & n \end{pmatrix}^{-1} \begin{pmatrix} \sum x_i^2 y_i \\ \sum x_i y_i \\ \sum y_i \end{pmatrix}.$$

Empirically, the fitted curve does not appear to have sufficient rise and fall near the peak. An analytic curve that provides better characteristics in this regard is an exponential curve, such as a Gaussian curve. A simple method for performing a Gaussian-like fit is to assume that the form of the curve is given by $$y = e^{ax^2 + bx + c},$$

in which case the quadratic equations above can be utilized by forming y', where y'=lny.

Assuming that the exponential curve is the preferred data fitting method, the robustness of the curve fit is examined in two ways: with respect to shifts in the wavelength and with respect to errors in the signal amplitude.

To examine the sensitivity of the analytical peak location when the window from which the curve fitting is performed is altered to fall 10 sampling intervals to the left or to the right of the true maxima. The resulting shift in mathematically-determined peak location is shown in Table 3. The conclusion to be derived is that the peak location is reasonably robust with respect to the particular window chosen: for a shift of approximately 1.5 nm, the corresponding peak location changed by only <0.06 nm, or 4 parts in one hundred sensitivity.

To examine the sensitivity of the peak location with respect to noise in the data, a signal free of noise must be defined, and then incremental amounts of noise is added to the signal and the impact of this noise on the peak location is examined. The ideal signal, for purposes of this experiment, is the average of 10 resonant spectra acquisitions.

Gaussian noise of varying degrees is superimposed on the ideal signal. For each such manufactured noisy signal, the peak location is estimated using the $2^{nd}$-order exponential curve fit. This is repeated 25 times, so that the average, maximum, and minimum peak locations are tabulated. This is repeated for a wide range of noise variances—from a variance of 0 to a variance of 750.

TABLE 3

Comparison of peak location as a function of window location

| Shift | Window | Peak Location |
|---|---|---|
| □ = −10 bins | 771.25-782.79 nm | 778.8221 nm |
| □ = 0 bins | 772.70-784.23 nm | 778.8887 nm |
| □ = +10 bins | 774.15-785.65 nm | 7778.9653 nm |

The conclusion of this experiment is that the peak location estimation routine is extremely robust to noisy signals. In one embodiment, the entire range of peak locations is only 1.5 nm, even with as much random noise variance of 750 superimposed—an amount of noise that is substantially greater that what has been observed on the biosensor thus far. The average peak location, despite the level of noise, is within 0.1 nm of the ideal location.

Based on these results, a basic algorithm for mathematically determining the peak location of a calorimetric resonant biosensor is as follows:
1. Input data $x_i$ and $y_i$, i=1, ... , n
2. Find maximum
   a. Find k such that $y_k \geq y_i$ for all i≠k
3. Check that maximum is sufficiently high
   a. Compute mean $\bar{y}$ and standard deviation σ of sample
   b. Continue only if $(y_k-\bar{y})/\sigma >$ UserThreshold
4. Define curve-fit region of 2w+1 bins (w defined by the user)
   a. Extract $x_i$, $k-w \leq i \leq k+w$
   b. Extract $y_i$, $k-w \leq i \leq k+w$
5. Curve fit
   a. $g_i = \ln y_i$
   b. Perform $2^{nd}$-order polynomial fit to obtain $g'_i$ defined on $x_i, k-w \leq i \leq k+w$ c. Polynomial fit returns coefficients a, b, c of form $ax^2+bx+c$
   d. Exponentiate: $y'_i = e^{g'_i}$
6. Output
   a. Peak location p given by $x_p = -b/2a$
   b. Peak value given by $y'_p(x_p)$ In summary, a robust peak determination routine has been demonstrated; the statistical results indicate significant insensitivity to the noise in the signal, as well as to the windowing procedure that is used. These results lead to the conclusion that, with reasonable noise statistics, that the peak location can be consistently determined in a majority of cases to within a fraction of a nm, perhaps as low as 0.1 to 0.05 nm.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description. Consequently, while the present invention has been described with reference to particular embodiments, modifications of structure, sequence, materials and the like apparent to those skilled in the art would still fall within the scope of the invention.

We claim:

1. A method of measuring biochemical surface interactions of a biosensor, said method comprising the steps of:
   incubating said biosensor at a predetermined temperature;
   providing a dual fiber optic probe with at least one illuminating fiber that is optically coupled to a light source, said illuminating fiber directing light towards a first surface of said biosensor;
   providing at least one detecting fiber, said at least one detecting fiber detecting light reflected from said first surface of the biosensor;
   optically coupling said at least one detecting fiber to a spectrometer; and
   analyzing said reflected light from said first surface of said biosensor.

2. The invention of claim 1 wherein said analyzing step comprises determining a Peak Wavelength Value of said reflected light.

3. The invention of claim 1 wherein said biosensor further comprises a second surface opposite said first surface, said second surface having a sample placed thereon and wherein the method further comprises step of generating a two-dimensional Peak Wavelength Value map of said second sensor surface.

4. The invention of claim 1 wherein said spectrometer includes a one dimensional charge coupled device.

5. The invention of claim 3 wherein said two-dimensional Peak Wavelength Value map is generated by said spectrometer.

6. The invention of claim 1 further including a step of providing a software interface that assists in controlling said spectrometer.

7. The invention of claim 6 further comprising the step of generating with said software interface a visual representation of a Peak Wavelength Value of said reflected light.

* * * * *

UNITED STATES PATENT AND TRADEMARK OFFICE
CERTIFICATE OF CORRECTION

| | |
|---|---|
| PATENT NO. | : 7,301,628 B2 |
| APPLICATION NO. | : 11/404430 |
| DATED | : November 27, 2007 |
| INVENTOR(S) | : Cunningham et al. |

It is certified that error appears in the above-identified patent and that said Letters Patent is hereby corrected as shown below:

Col. 7, Line 31, "calorimetric" should read --colorimetric--.

Col. 23, Line 63, "calorimetric" should read --colorimetric--.

Signed and Sealed this

Nineteenth Day of August, 2008

JON W. DUDAS
*Director of the United States Patent and Trademark Office*